United States Patent
Sasikumar et al.

(10) Patent No.: US 11,274,123 B2
(45) Date of Patent: *Mar. 15, 2022

(54) 1,2,4-OXADIAZOLE COMPOUNDS AS INHIBITORS OF CD47 SIGNALLING

(71) Applicant: AURIGENE DISCOVERY TECHNOLOGIES LIMITED, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN); Chennakrishnareddy Gundala, Bangalore (IN)

(73) Assignee: AURIGENE DISCOVERY TECHNOLOGIES LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 16/245,860

(22) Filed: Jan. 11, 2019

(65) Prior Publication Data

US 2019/0218252 A1    Jul. 18, 2019

(30) Foreign Application Priority Data

Jan. 12, 2018 (IN) .............................. 201841001438

(51) Int. Cl.
| | | |
|---|---|---|
| *A61K 38/00* | (2006.01) | |
| *C07K 5/02* | (2006.01) | |
| *C07D 413/14* | (2006.01) | |
| *C07D 413/04* | (2006.01) | |
| *C07D 271/06* | (2006.01) | |
| *C07D 413/12* | (2006.01) | |
| *A61P 9/10* | (2006.01) | |
| *A61P 25/28* | (2006.01) | |
| *A61P 35/02* | (2006.01) | |
| *A61P 31/22* | (2006.01) | |
| *A61P 31/18* | (2006.01) | |
| *A61P 31/04* | (2006.01) | |
| *A61P 31/10* | (2006.01) | |
| *A61P 31/16* | (2006.01) | |

(52) U.S. Cl.
CPC .............. *C07K 5/0215* (2013.01); *A61P 9/10* (2018.01); *A61P 25/28* (2018.01); *A61P 35/02* (2018.01); *C07D 271/06* (2013.01); *C07D 413/04* (2013.01); *C07D 413/12* (2013.01); *C07D 413/14* (2013.01); *A61K 38/00* (2013.01); *A61P 31/04* (2018.01); *A61P 31/10* (2018.01); *A61P 31/16* (2018.01); *A61P 31/18* (2018.01); *A61P 31/22* (2018.01)

(58) Field of Classification Search
None
See application file for complete search history.

(56) References Cited

U.S. PATENT DOCUMENTS

| 7,528,148 B2 * | 5/2009 | Allen ...................... A61P 25/28 514/303 |
| 2007/0225332 A1 * | 9/2007 | Gu ....................... C07D 277/34 514/332 |
| 2016/0304609 A1 | 10/2016 | Liu et al. |
| 2017/0081407 A1 | 3/2017 | Grosveld et al. |

FOREIGN PATENT DOCUMENTS

| WO | 2015033299 A1 | 3/2015 |
| WO | 2016142833 A1 | 9/2016 |
| WO | 2016142886 A2 | 9/2016 |
| WO | 2016188449 A1 | 12/2016 |
| WO | 2017194627 A1 | 11/2017 |
| WO | 2017194634 A1 | 11/2017 |

OTHER PUBLICATIONS

Szabo, Cellular Immunology, vol. 164, Issue 2, Sep. 1995, pp. 182-188 (Year: 1995).*
Stephen M. Berge, et al., Pharmaceutical Salts, Journal of Pharmaceutical Sciences (Jan. 1977) vol. 66, No. 1, p. 1-19.
Mark. P. Chao, et al. The CD47-SIRPα Pathway in Cancer Immune Evasion and Potential Therapeutic Implications, Curr Opin Immunol (Apr. 2012) vol. 24, No. 2, p. 225-232.
Qiangguo Gao et al., Blockade of CD47 Ameliorates Autoimmune Inflammation in CNS by Suppressing IL-1-Triggered Infiltration of Pathogenic Th17 Cells, Journal of Autoimmunity (May 2016) vol. 69, p. 74-85.
Yoko Kojima, et al., CD47-Blocking Antibodies Restore Phagocytosis and Prevent Atherosclerosis, Nature (Aug. 2016) vol. 536, No. 7614, p. 86-90.

* cited by examiner

*Primary Examiner* — Satyanarayana R Gudibande
(74) *Attorney, Agent, or Firm* — Duane Morris LLP; Thomas J. Kowalski; Deborah L. Lu

(57) ABSTRACT

The present invention relates to compounds of formula (I), compositions, methods and uses involving the said formula (I) that inhibit CD47 signaling pathway. The present invention also relates to methods of making such compounds and their uses for the treatment of diseases or disorders mediated by CD47.

17 Claims, No Drawings

1,2,4-OXADIAZOLE COMPOUNDS AS INHIBITORS OF CD47 SIGNALLING

CROSS-REFERENCE TO RELATED APPLICATIONS

This non-provisional application claims benefit under 35 U.S.C. § 119(a) of Indian provisional application number 201841001438, filed on Jan. 12, 2018, the entirety of which is hereby incorporated by reference.

BACKGROUND OF THE INVENTION

Field of the Invention

The present invention relates to therapeutically useful 1,2,4-oxadiazole compounds of formula (I) as CD47 signaling pathway inhibitors. The invention also relates to pharmaceutical compositions comprising said compounds or a pharmaceutically acceptable salt or an amide or an ester, or a stereoisomer thereof.

Description of the Related Art

Antagonist antibodies targeting CTLA-4, PD-1 and PD-L1 impact adaptive immune system, predominantly T cells, and have shown impressive clinical efficacy across a wide range of cancers. Despite the success of these T-cell based checkpoint inhibitors in a subset of patients, the majority of patients still do not show adequate clinical response. Checkpoint proteins on cells of innate immune system are also known to regulate immune response. Among the innate immune checkpoint proteins, CD47 is up-regulated in a wide range of malignancies that negatively regulates macrophage-mediated phagocytosis. CD47 mediated phagocytosis are primarily through interactions with SIRP1α expressed on macrophages. Blockade of SIRP1α/CD47 has been shown to dramatically enhance tumor cell phagocytosis and dendritic cells maturation for better antigen presentation leading to substantially improved antitumor responses in preclinical models of cancer (M. P. Chao et al. Curr Opin Immunol. 2012 (2): 225-232).

CD-47 as a Target to Eliminate Tumor Cells

CD47 also known as integrin associated protein (IAP), ovarian cancer antigen OA3, Rh-related antigen and MERG, is a transmembrane protein that, in humans, is encoded by the CD47 gene. CD47 belongs to the immunoglobulin superfamily and partners with membrane integrins and also binds the ligands thrombospondin-1 (TSP-1) and signal-regulatory protein alpha (SIRPα). CD47 is best known for its pivotal role in preventing phagocytic removal of healthy cells by binding to phagocyte-expressed signal regulatory protein alpha (SIRPα). SIRPα, an inhibitory protein expressed on macrophages, once triggered, suppresses phagocytosis of CD47-expressing cells. This CD47/SIRPα axis is an important homeostatic mechanism preventing removal of healthy normal cells that express CD47. Reversely, down-regulation of CD47 on damaged, aged and superfluous cells ensures their timely removal.

CD47 is expressed on virtually all non-malignant cells, and blocking the CD47 or the loss of CD47 expression or changes in membrane distribution can serve as markers of aged or damaged cells, particularly on red blood cells (RBC). Alternatively, blocking SIRPα also allows engulfment of targets that are not normally phagocytosed, for those cells where pre-phagocytic signals are also present. CD47 is a broadly expressed transmembrane glycoprotein with a single Ig-like domain and five membrane spanning regions, which functions as a cellular ligand for SIRPα with binding mediated through the $NH_2$-terminal V-like domain of SIRPα. SIRPα is expressed primarily on myeloid cells, including macrophages, granulocytes, myeloid dendritic cells (DCs), mast cells, and their precursors, including hematopoietic stem cells.

CD47 is also constitutively upregulated on a number of cancers such as Non-Hodgkin Lymphoma (NHL), Acute myeloid leukemia (AML), breast, colon, glioblastoma, glioma, ovarian, bladder and prostate cancers. Overexpression of CD47 by tumor cells, which efficiently helps them to escape immune surveillance and killing by innate immune cells.

It has been shown that CD47 may be considered as potential target for the treatment of atherosclerosis. Because, the process of atherogenesis i.e., the formation of atheromas on the wall of arteries, is associated with upregulation of CD47 which renders malignant cells resistant to programmed cell removal, or 'efferocytosis'. This effect of efferocytosis, is reversed upon administration of CD47-blocking antibodies which normalizes the clearance of diseased vascular tissue, and ameliorates atherosclerosis in multiple mouse models (Kojima Y, et al., Nature. 2016 Aug. 4; 536 (7614): 86-90). Further, it has been reported that blockade of CD47 with CD47-Fc fusion protein is effective in regulating Experimental autoimmune encephalomyelitis (EAE), an animal model for multiple sclerosis (MS), pathology and provides a potential therapeutic target in preventing and treating MS (Gao Q et al., J Autoimmun. 2016 May; 69: 74-85).

Several publications such as US20160304609, WO2016188449, US20170081407, WO2017194627 and WO2017194634 disclosing compounds (i.e., antibodies and peptides) that modulate CD47 have been published.

Despite several recent advances made, there is still an unmet need for effective CD47 inhibitors that block SIRP1α-CD47 signaling pathway for the treatment of cancers that are mediated by the elevated levels of CD47 expression.

SUMMARY OF INVENTION

The present invention provides the compounds and their pharmaceutically acceptable salts. These compounds are capable of suppressing and/or inhibiting the CD47 signaling pathway.

In one aspect, the present invention provides compounds of formula (I):

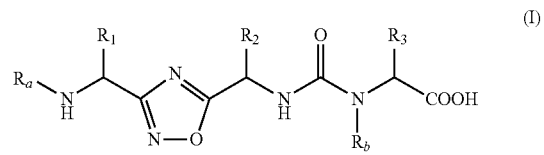

or a pharmaceutically acceptable salt or an amide or an ester, or a stereoisomer thereof;

wherein, $R_a$ is hydrogen or acyl; and $R_1$ represents hydrogen, —$(CH_2)_2CONH_2$, —$(CH_2)_2COOH$, —$CH_2COOH$, —$(CH_2)_3NH(C=NH)NH_2$, —$(CH_2)_4NH_2$, —$CH_2CONH_2$, —$CH(CH_3)$—$CH_2$—$CH_3$, —$CH_2$-aryl, or —$CH_2$-heteroaryl; wherein the said aryl and heteroaryl are unsubstituted; or $R_a$ and $R_1$, together with the atoms to which they are attached form pyrrolidine ring optionally substituted with oxo group;

$R_2$ represents hydrogen, —$CH_2$—OH, —$(CH_2)_3$NHC(=NH)$NH_2$, —$(CH_2)_2$CONH$_2$, —$(CH_2)_2$COOH, —$CH_2$-aryl, or —$CH_2$-heteroaryl; wherein the said aryl and heteroaryl are unsubstituted;

$R_b$ is hydrogen; and $R_3$ represents hydrogen, —$CH_2$-aryl, —$(CH_2)_3$NHC(=NH)$NH_2$, —$CH_2$COOH, —CH(CH$_3$)—CH$_2$—CH$_3$, —CH$_2$—CH(CH$_3$)$_2$, —(CH$_2$)$_2$CONH$_2$, —(CH$_2$)$_2$COOH, —(CH$_2$)$_4$NH$_2$ or —CH$_2$-heteroaryl; wherein the said aryl and heteroaryl are unsubstituted; or $R_b$ and $R_3$, together with the atoms to which they are attached form pyrrolidine ring.

In another aspect, the present invention relates to pharmaceutical compositions comprising a compound of formula (I) or a pharmaceutically acceptable salt or an amide or an ester, or a stereoisomer thereof and processes for preparing such compositions.

Yet another aspect of the present invention provides a method of treating diseases or disorders mediated by CD47 which comprises administering a compound of formula (I) or a pharmaceutically acceptable salt or an amide or an ester, or a stereoisomer thereof.

DETAILED DESCRIPTION OF THE INVENTION

The present invention provides 1,2,4-oxadiazole compounds and their derivatives as therapeutic agents useful for treatment of disorders mediated by CD-47.

Each embodiment is provided by way of explanation of the invention, and not by way of limitation of the invention. In fact, it will be apparent to those skilled in the art that various modifications and variations can be made to the compounds, compositions, and methods described herein without departing from the scope or spirit of the invention. For instance, features illustrated or described as part of one embodiment can be applied to another embodiment to yield a still further embodiment. Thus, it is intended that the present invention include such modifications and variations and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In certain embodiments, the present invention provides a compound of formula (I):

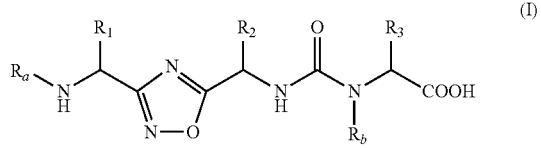

or a pharmaceutically acceptable salt or an amide or an ester, or a stereoisomer thereof;
wherein, $R_a$ is hydrogen or acyl; and $R_1$ represents hydrogen, —(CH$_2$)$_2$CONH$_2$, —(CH$_2$)$_2$COOH, —CH$_2$COOH, —(CH$_2$)$_3$NH(C=NH)NH$_2$, —(CH$_2$)$_4$NH$_2$, —CH$_2$CONH$_2$, —CH(CH$_3$)—CH$_2$—CH$_3$, —CH$_2$-aryl, or —CH$_2$-heteroaryl; wherein the said aryl and heteroaryl are unsubstituted; or $R_a$ and $R_1$, together with the atoms to which they are attached form pyrrolidine ring optionally substituted with oxo group;

$R_2$ represents hydrogen, —CH$_2$—OH, —(CH$_2$)$_3$NHC(=NH)NH$_2$, —(CH$_2$)$_2$CONH$_2$, —(CH$_2$)$_2$COOH, —CH$_2$-aryl, or —CH$_2$-heteroaryl; wherein the said aryl and heteroaryl are unsubstituted;

$R_b$ is hydrogen; and $R_3$ represents hydrogen, —CH$_2$-aryl, —(CH$_2$)$_3$NHC(=NH)NH$_2$, —CH$_2$COOH, —CH(CH$_3$)—CH$_2$—CH$_3$, —CH$_2$—CH(CH$_3$)$_2$, —(CH$_2$)$_2$CONH$_2$, —(CH$_2$)$_2$COOH, —(CH$_2$)$_4$NH$_2$ or —CH$_2$-heteroaryl; wherein the said aryl and heteroaryl are unsubstituted; or $R_b$ and $R_3$, together with the atoms to which they are attached form pyrrolidine ring.

In certain other embodiments, the present invention provides a compound of formula (I):
wherein, $R_a$ is hydrogen; and $R_1$ represents hydrogen, —(CH$_2$)$_2$CONH$_2$, —(CH$_2$)$_2$COOH, —(CH$_2$)$_3$NH(C=NH)NH$_2$, —(CH$_2$)$_4$NH$_2$, —CH$_2$CONH$_2$, —CH$_2$-aryl, or —CH$_2$-heteroaryl; or $R_a$ and $R_1$, together with the atoms to which they are attached form pyrrolidine ring;

$R_2$ represents hydrogen, —(CH$_2$)$_3$NHC(=NH)NH$_2$, —(CH$_2$)$_2$CONH$_2$, —(CH$_2$)$_2$COOH, —CH$_2$-aryl, or —CH$_2$-heteroaryl;

$R_b$ is hydrogen; and $R_3$ represents hydrogen, —CH$_2$-aryl, —(CH$_2$)$_3$NHC(=NH)NH$_2$, —(CH$_2$)$_2$CONH$_2$, —(CH$_2$)$_2$COOH, —(CH$_2$)$_4$NH$_2$ or —CH$_2$-heteroaryl; or $R_b$ and $R_3$, together with the atoms to which they are attached form pyrrolidine ring.

In certain embodiments, the present invention provides a compound of formula (I): wherein, $R_a$ is hydrogen or acyl; and $R_1$ represents hydrogen, —CH$_2$COOH, —(CH$_2$)$_3$NH(C=NH)NH$_2$, —CH$_2$CONH$_2$, —CH(CH$_3$)—CH$_2$—CH$_3$, or —CH$_2$-heteroaryl; wherein the said aryl and heteroaryl are unsubstituted; or $R_a$ and $R_1$, together with the atoms to which they are attached form pyrrolidine ring optionally substituted with oxo group;

$R_2$ represents hydrogen, —CH$_2$—OH or —CH$_2$-heteroaryl; wherein the said heteroaryl is unsubstituted;

$R_b$ is hydrogen; and $R_3$ represents —CH$_2$-aryl, —CH(CH$_3$)$_2$, —CH$_2$COOH, —CH(CH$_3$)—CH$_2$—CH$_3$, —CH$_2$—CH(CH$_3$)$_2$, —(CH$_2$)$_2$COOH, or —(CH$_2$)$_4$NH$_2$; wherein the said aryl is unsubstituted;

In certain embodiments, the present invention provides a compound of formula (I):
wherein, $R_a$ is hydrogen or acyl; and $R_1$ represents —(CH$_2$)$_2$CONH$_2$, —(CH$_2$)$_4$NH$_2$, —(CH$_2$)$_3$NH(C=NH)NH$_2$ or —CH$_2$-heteroaryl; wherein the said heteroaryl is unsubstituted;

$R_2$ represents; —(CH$_2$)$_3$NHC(=NH)NH$_2$, —(CH$_2$)$_2$CONH$_2$, —(CH$_2$)$_2$COOH, or —CH$_2$-aryl; wherein the said aryl is unsubstituted;

$R_b$ is hydrogen; and $R_3$ represents hydrogen, —(CH$_2$)$_2$CONH$_2$, or —CH$_2$-heteroaryl; wherein the said heteroaryl is unsubstituted; or $R_b$ and $R_3$, together with the atoms to which they are attached form pyrrolidine ring.

In certain embodiments, $R_1$ represents hydrogen, —(CH$_2$)$_2$CONH$_2$, —(CH$_2$)$_2$COOH, —(CH$_2$)$_3$NH(C=NH)NH$_2$, —(CH$_2$)$_4$NH$_2$, —CH$_2$CONH$_2$, CH(CH$_3$)—CH$_2$—CH$_3$, —CH$_2$-aryl, or —CH$_2$— heteroaryl; wherein the said heteroaryl is unsubstituted.

In certain embodiments, $R_1$ represents hydrogen, —(CH$_2$)$_2$CONH$_2$, —(CH$_2$)$_2$COOH, —(CH$_2$)$_3$NH(C=NH)

$NH_2$, —$(CH_2)_4NH_2$, —$CH_2CONH_2$, $CH(CH_3)$—$CH_2$—$CH_3$, —$CH_2$-phenyl, —$CH_2$-indolyl, or —$CH_2$-imidazolyl.

In certain embodiments, $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH_2CONH_2$, —$CH_2$-phenyl, or —$CH_2$-imidazolyl.

In certain embodiments, $R_1$ represents —$(CH_2)_2CONH_2$, —$(CH_2)_2COOH$, —$(CH_2)_3NH(C=NH)NH_2$, —$(CH_2)_4NH_2$, —$CH_2CONH_2$, —$CH_2$-phenyl, or —$CH_2$-imidazolyl.

In certain embodiments, $R_1$ represents —$(CH_2)_2CONH_2$, —$(CH_2)_2COOH$, —$(CH_2)_3NH(C=NH)NH_2$, —$(CH_2)_4NH_2$, or —$CH_2$-imidazolyl.

In certain embodiments, $R_1$ represents —$(CH_2)_2CONH_2$, —$(CH_2)_2COOH$, —$(CH_2)_3NH(C=NH)NH_2$, —$(CH_2)_4NH_2$, —$CH_2CONH_2$, or —$CH_2$-phenyl.

In certain embodiments, $R_1$ represents —$(CH_2)_2CONH_2$, —$(CH_2)_2COOH$, —$(CH_2)_3NH(C=NH)NH_2$, or —$(CH_2)_4NH_2$.

In certain embodiments, $R_1$ represents —$(CH_2)_3NH(C=NH)NH_2$, —$(CH_2)_2CONH_2$, or —$(CH_2)_2COOH$.

In certain embodiments, $R_1$ represents —$(CH_2)_2COOH$, —$CH_2COOH$, —$CH_2CONH_2$, —$CH(CH_3)$—$CH_2$—$CH_3$ or —$CH_2$-aryl; wherein the said aryl is unsubstituted.

In certain embodiments, $R_1$ represents —$(CH_2)_2CONH_2$, or —$(CH_2)_2COOH$.

In certain embodiments, $R_a$ is hydrogen. In certain embodiments, $R_a$ is acyl. In certain embodiments, $R_a$ is acetyl.

In another embodiments, in formula (I), $R_a$ and $R_1$, together with the atoms to which they are attached form pyrrolidine ring optionally substituted with oxo group.

In certain embodiments, $R_2$ represents hydrogen, —$CH_2$—$OH$, —$(CH_2)_3NHC(=NH)NH_2$, —$(CH_2)_2CONH_2$, —$(CH_2)_2COOH$, —$CH_2$-phenyl, —$CH_2$-indolyl, or —$CH_2$-imidazolyl.

In certain embodiments, $R_2$ represents hydrogen, —$(CH_2)_3NHC(=NH)NH_2$, —$(CH_2)_2CONH_2$, —$(CH_2)_2COOH$, —$CH_2$-phenyl, or —$CH_2$-imidazolyl.

In certain embodiments, $R_2$ represents hydrogen, —$(CH_2)_3NHC(=NH)NH_2$, —$(CH_2)_2CONH_2$, —$(CH_2)_2COOH$, or —$CH_2$-phenyl.

In certain embodiments, $R_2$ represents hydrogen, —$(CH_2)_3NHC(=NH)NH_2$, —$(CH_2)_2COOH$, or —$CH_2$-phenyl.

In certain embodiments, $R_2$ represents hydrogen, —$(CH_2)_3NHC(=NH)NH_2$, —$(CH_2)_2CONH_2$, or —$(CH_2)_2COOH$.

In certain embodiments, $R_2$ represents hydrogen, —$(CH_2)_3NHC(=NH)NH_2$, —$(CH_2)_2CONH_2$, or —$(CH_2)_2COOH$.

In certain embodiments, $R_2$ represents hydrogen, —$(CH_2)_3NHC(=NH)NH_2$, —$(CH_2)_2CONH_2$, —$(CH_2)_2COOH$, or —$CH_2$-phenyl.

In certain embodiments, $R_2$ represents hydrogen or —$(CH_2)_3NHC(=NH)NH_2$.

In certain embodiments, $R_3$ represents hydrogen, —$(CH_2)_3NHC(=NH)NH_2$, —$CH_2COOH$, —$CH(CH_3)$—$CH_2$—$CH_3$, —$CH_2$—$CH(CH_3)_2$, —$(CH_2)_2CONH_2$, —$(CH_2)_2COOH$, —$(CH_2)_4NH_2$, —$CH_2$-phenyl, —$CH_2$-indolyl, or —$CH_2$-imidazolyl.

In certain embodiments, $R_3$ represents hydrogen, —$CH_2$-phenyl, —$(CH_2)_3NHC(=NH)NH_2$, —$(CH_2)_2CONH_2$, —$(CH_2)_2COOH$, —$CH(CH_3)$—$CH_2$—$CH_3$, —$CH_2$—$CH(CH_3)_2$, —$(CH_2)_4NH_2$ or —$CH_2$— imidazolyl.

In certain embodiments, $R_3$ represents hydrogen, —$CH_2$-phenyl, —$(CH_2)_3NHC(=NH)NH_2$, —$(CH_2)_2CONH_2$, —$(CH_2)_2COOH$, —$(CH_2)_4NH_2$ or —$CH_2$-heteroaryl; wherein the said heteroaryl is unsubstituted.

In certain embodiments, $R_3$ represents hydrogen, —$CH_2$-phenyl, —$(CH_2)_3NHC(=NH)NH_2$, —$(CH_2)_2CONH_2$, —$(CH_2)_2COOH$, —$(CH_2)_4NH_2$ or —$CH_2$-imidazolyl.

In certain embodiments, $R_3$ represents hydrogen, —$CH_2$-phenyl, —$(CH_2)_3NHC(=NH)NH_2$, —$(CH_2)_2CONH_2$, —$(CH_2)_2COOH$, or —$(CH_2)_4NH_2$.

In certain embodiments, $R_3$ represents hydrogen, —$CH_2$-phenyl, —$(CH_2)_3NHC(=NH)NH_2$, —$(CH_2)_2CONH_2$, or —$(CH_2)_2COOH$.

In certain embodiments, $R_3$ represents hydrogen, —$CH(CH_3)$—$CH_2$—$CH_3$, —$CH_2$—$CH(CH_3)_2$, $CH_3COOH$ or —$CH_2$-heteroaryl; wherein the said heteroaryl is unsubstituted.

In certain embodiments, $R_3$ represents —$CH_2$-phenyl, —$(CH_2)_3NHC(=NH)NH_2$, —$(CH_2)_2COOH$ or —$(CH_2)_4NH_2$;

In certain embodiments, $R_b$ and $R_3$, together with the atoms to which they are attached form pyrrolidine ring.

In another embodiments, the present invention provides a compound of formula (I):
wherein;

$R_a$ is hydrogen or acyl; and $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH_2CONH_2$, —$CH(CH_3)$—$CH_2$—$CH_3$, —$CH_2$-phenyl, —$CH_2$-indolyl, or —$CH_2$-imidazolyl; wherein the said phenyl, indolyl and imidazolyl are unsubstituted; or $R_a$ and together with the atoms to which they are attached form pyrrolidine ring optionally substituted with oxo group;

$R_2$ represents hydrogen, $CH_2$—$OH$, —$(CH_2)_3NHC(=NH)NH_2$, —$(CH_2)_2CONH_2$, —$(CH_2)_2COOH$, —$CH_2$-phenyl, —$CH_2$-indolyl, or —$CH_2$-imidazolyl; wherein the said imidazolyl is unsubstituted.

$R_b$ is hydrogen; and $R_3$ represents hydrogen, —$CH_2$-phenyl, —$(CH_2)_3NHC(=NH)NH_2$, —$(CH_2)_2CONH_2$, —$CH_2COOH$, —$CH_2$—$CH(CH_3)_2$, —$(CH_2)_2CONH_2$, —$(CH_2)_2COOH$, —$(CH_2)_4NH_2$, —$CH_2$— indolyl, or —$CH_2$-imidazolyl; wherein the said phenyl, indolyl and imidazolyl are unsubstituted; or $R_b$ and $R_3$, together with the atoms to which they are attached form pyrrolidine ring.

In certain embodiments, the present invention provides compound of formula (I), wherein $R_a$ is hydrogen; $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH_2CONH_2$, —$CH_2$-phenyl, or —$CH_2$-imidazolyl; or $R_a$ and $R_1$, together with the atoms to which they are attached form pyrrolidine ring;

$R_2$ represents hydrogen, —$(CH_2)_3NHC(=NH)NH_2$, —$(CH_2)_2CONH_2$, —$(CH_2)_2COOH$, —$CH_2$— phenyl, or —$CH_2$-imidazolyl;

$R_b$ is hydrogen; $R_3$ represents hydrogen, —$CH_2$-phenyl, —$(CH_2)_3NHC(=NH)NH_2$, —$(CH_2)_2CONH_2$, —$(CH_2)_2COOH$, —$(CH_2)_4NH_2$ or —$CH_2$-imidazolyl; or $R_b$ and $R_3$, together with the atoms to which they are attached form pyrrolidine ring.

In certain embodiments, the compound is not one of

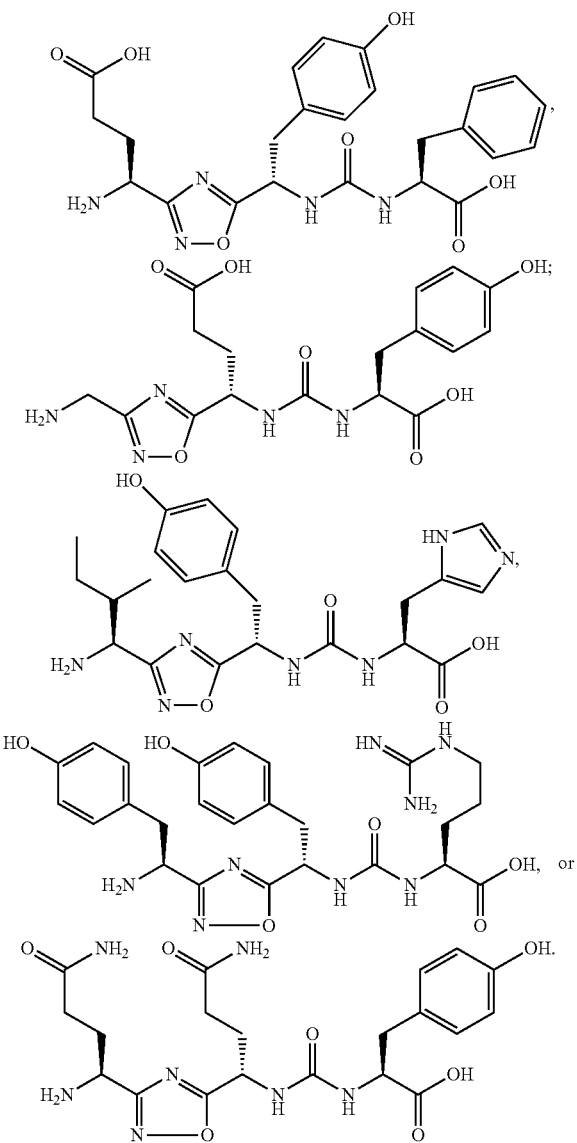

In certain embodiments, the present invention provides a compound of formula (IA):

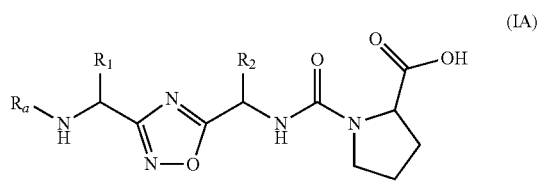

or a pharmaceutically acceptable salt or an amide or an ester, or a stereoisomer thereof;

wherein, $R_1$, $R_a$ and $R_2$ are as defined in compound of formula (I).

In certain embodiments, $R_1$ represents hydrogen, —$CH_2$—COOH, —$CH_2$—$CONH_2$, —$CH(CH_3)$—$CH_2$—$CH_3$, —$(CH_2)_2CONH_2$, —$(CH_2)_2COOH$, —$(CH_2)_3NH(C=NH)NH_2$, —$(CH_2)_4NH_2$, —$CH_2$-phenyl, —$CH_2$-indolyl or —$CH_2$-imidazolyl.

In certain embodiments, $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH_2$-phenyl, or —$CH_2$-imidazolyl.

In certain embodiments, $R_1$ represents —$(CH_2)_2CONH_2$, —$(CH_2)_2COOH$, —$(CH_2)_3NH(C=NH)NH_2$, or —$(CH_2)_4NH_2$.

In certain embodiments, $R_1$ represents —$(CH_2)_2CONH_2$, or —$(CH_2)_2COOH$.

In certain embodiments, $R_2$ represents hydrogen, —$CH_2$—OH—$(CH_2)_2CONH_2$, —$(CH_2)_3NHC(=NH)NH_2$, —$(CH_2)_2COOH$ or —$CH_2$-phenyl.

In certain embodiments, $R_2$ represents hydrogen, —$(CH_2)_3NHC(=NH)NH_2$, or —$(CH_2)_2COOH$.

In certain embodiments, $R_2$ represents hydrogen, —$(CH_2)_2CONH_2$, or —$(CH_2)_2COOH$.

In another embodiments, the present invention provides a compound of formula (IA): wherein $R_a$ is hydrogen; and $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH_2$-phenyl, or —$CH_2$-imidazolyl; and $R_2$ represents hydrogen, —$(CH_2)_3NHC(=NH)NH_2$, —$(CH_2)_2CONH_2$, —$(CH_2)_2COOH$, —$CH_2$— phenyl or —$CH_2$-imidazolyl.

In certain embodiments, the present invention provides a compound of formula (IA):
wherein;

$R_a$ is hydrogen; and $R_1$ represents hydrogen, —$CH_2$—COOH, —$CH_2$—$CONH_2$, —$CH(CH_3)$—$CH_2$—$CH_3$, —$(CH_2)_2CONH_2$, —$(CH_2)_2COOH$, —$(CH_2)_3NH(C=NH)NH_2$, —$(CH_2)_4NH_2$, —$CH_2$-phenyl, —$CH_2$— indolyl or —$CH_2$-imidazolyl; wherein the said phenyl, indolyl and imidazolyl are unsubstituted;

$R_2$ represents hydrogen, —$CH_2$—OH—$(CH_2)_2CONH_2$, —$(CH_2)_3NHC(=NH)NH_2$, —$(CH_2)_2COOH$ or —$CH_2$-phenyl; wherein the said phenyl is unsubstituted.

In another embodiments, the present invention provides a compound of formula (IA):
wherein;

$R_a$ is hydrogen; and $R_1$ represents hydrogen, —$(CH_2)_2CONH_2$, —$(CH_2)_2COOH$, —$(CH_2)_3NH(C=NH)NH_2$, —$CH_2COOH$, —$CH_2CONH_2$, —$(CH_2)_4NH_2$, —$CH(CH_3)$—$CH_2$—$CH_3$, —$CH_2$-phenyl, —$CH_2$-indolyl or —$CH_2$-imidazolyl; and $R_2$ represents hydrogen, —$CH_2$—OH, —$(CH_2)_3NHC(=NH)NH_2$, —$(CH_2)_2COOH$, —$CH_2$-phenyl, or —$CH_2$-imidazolyl.

In another embodiments, the present invention provides a compound of formula (IA):
wherein;

$R_a$ is hydrogen; and $R_1$ represents hydrogen, —$(CH_2)_2CONH_2$, —$(CH_2)_2COOH$, —$(CH_2)_3NH(C=NH)NH_2$, —$(CH_2)_4NH_2$, —$CH(CH_3)$—$CH_2$—$CH_3$, —$CH_2$-phenyl, or —$CH_2$-imidazolyl; and $R_2$ represents hydrogen, —$CH_2$—OH, —$(CH_2)_3NHC(=NH)NH_2$, —$(CH_2)_2COOH$, —$CH_2$-phenyl, or —$CH_2$-imidazolyl.

In another embodiments, the present invention provides a compound of formula (IA):
wherein $R_a$ is hydrogen; and $R_1$ represents —$(CH_2)_2CONH_2$, —$(CH_2)_2COOH$, —$(CH_2)_3NH(C=NH)NH_2$, or —$(CH_2)_4NH_2$ and $R_2$ represents hydrogen, —$(CH_2)_3NHC(=NH)NH_2$, —$(CH_2)_2COOH$, —$CH_2$-phenyl, or —$CH_2$— imidazolyl.

In certain embodiments, the compounds of formula (IA) are:
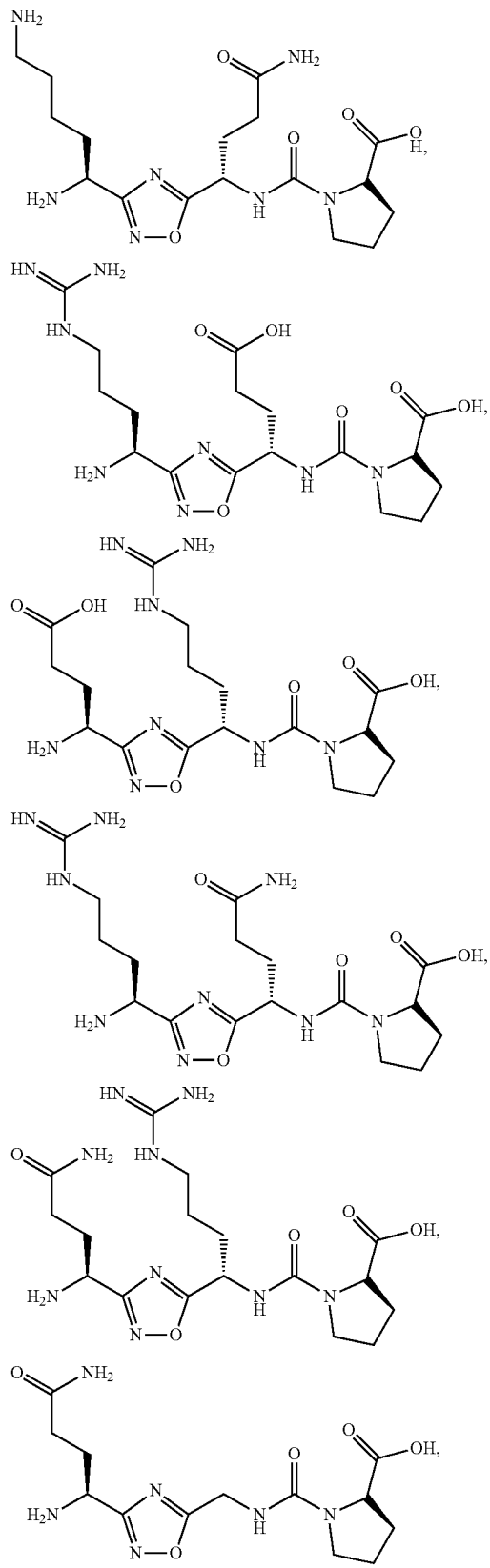

-continued
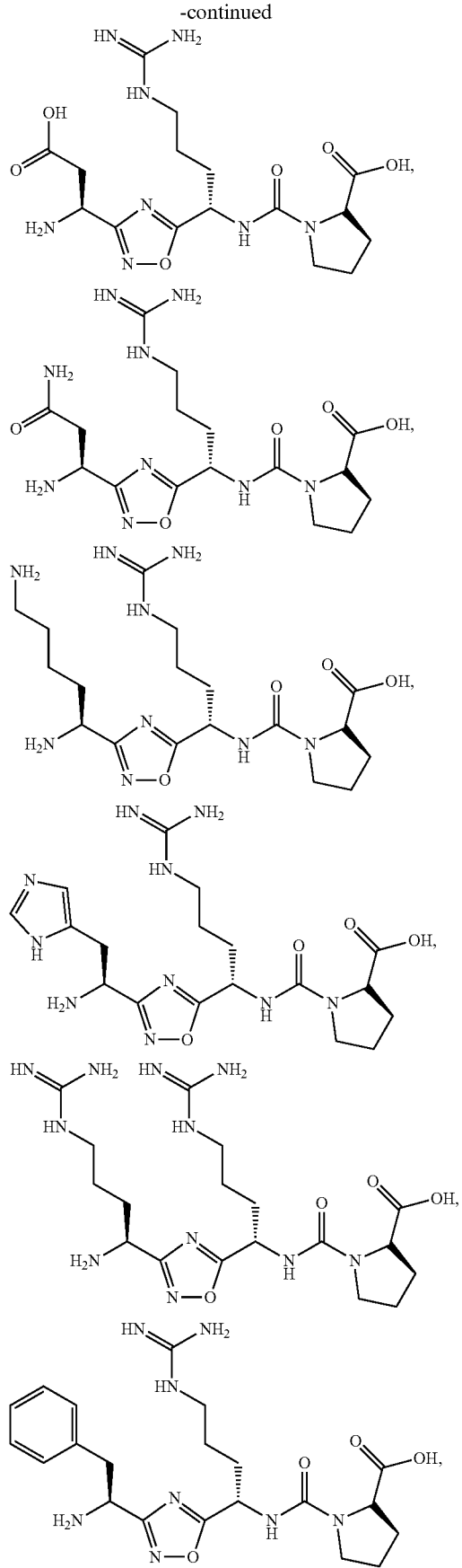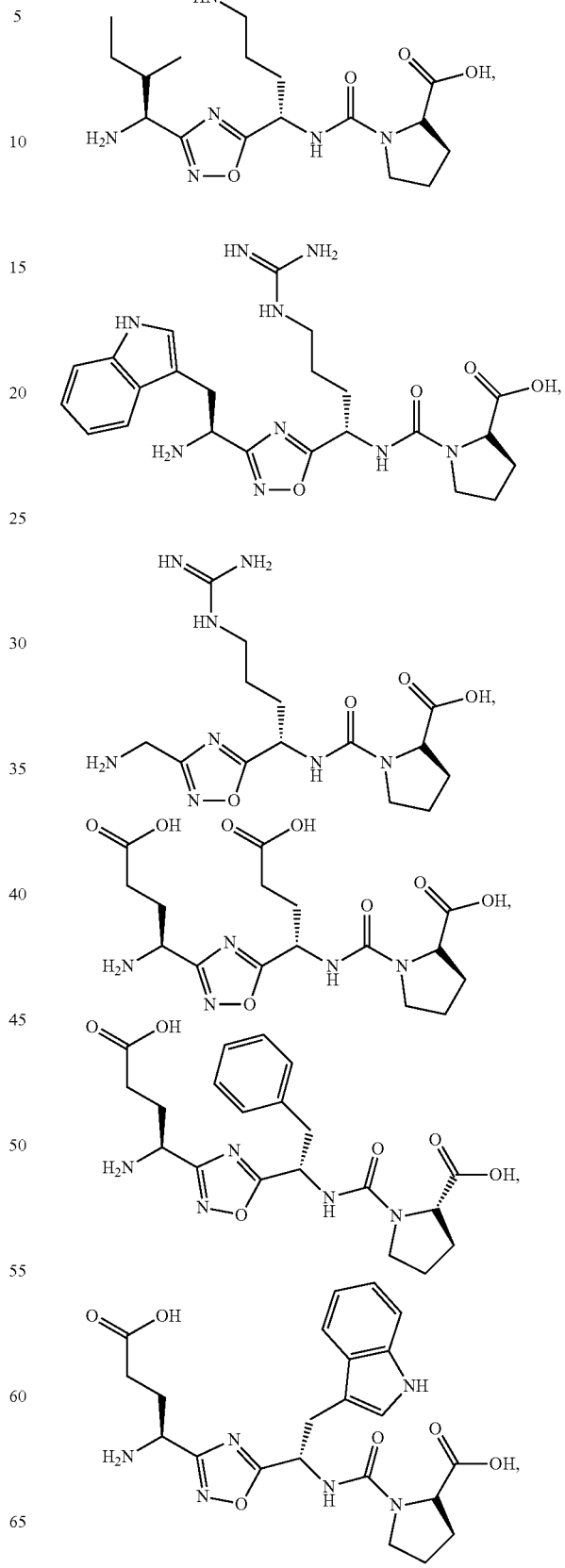

-continued

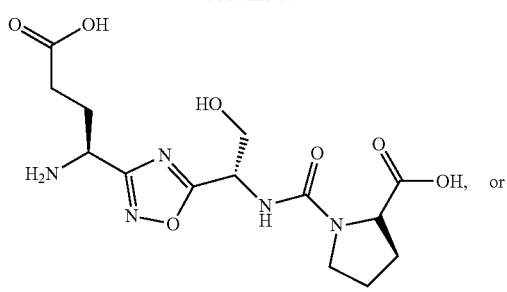

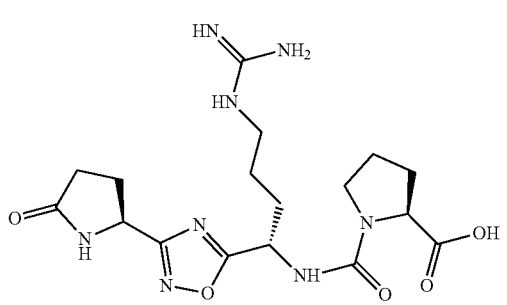

or a pharmaceutically acceptable salt or an amide or an ester, or a stereoisomer thereof.

In certain embodiments, the compounds of formula (I) are:

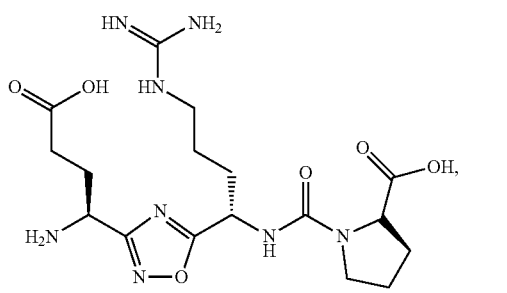

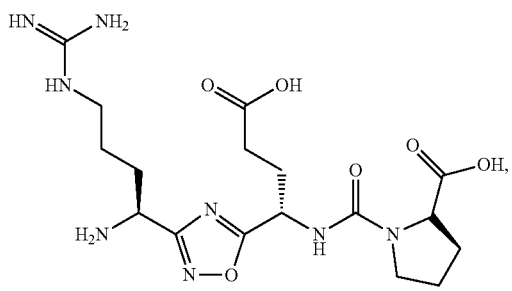

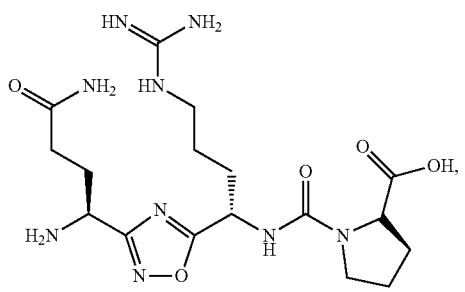

-continued

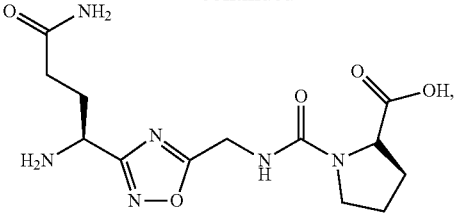

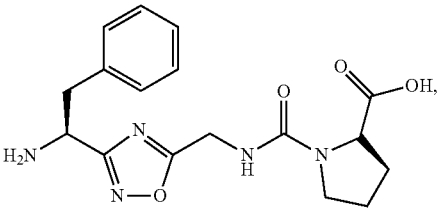

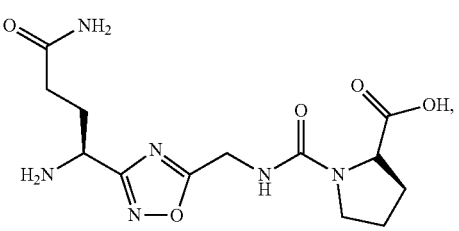

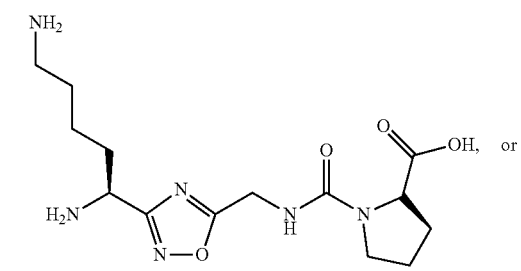

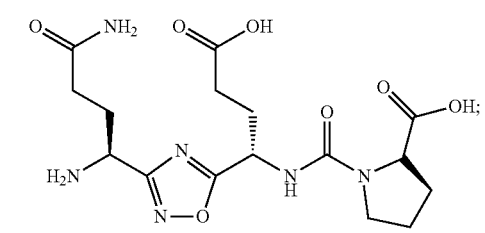

or a pharmaceutically acceptable salt or an amide or an ester, or a stereoisomer thereof;

In certain embodiments of the present invention, the compound of formula (IA) can also be written by showing the absolute stereochemistry thereof, as (IA)

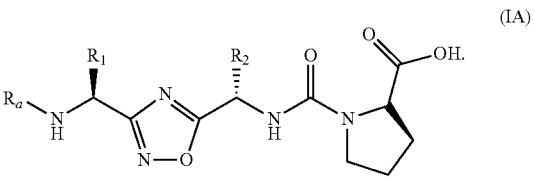

In certain embodiments, the present invention provides a compound of formula (IB):

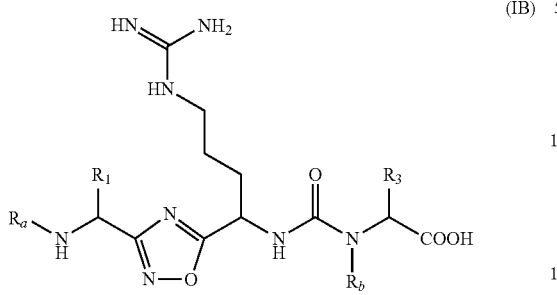

(IB)

or a pharmaceutically acceptable salt or an amide or an ester, or a stereoisomer thereof;
wherein, $R_1$, $R_a$, $R_b$ and $R_3$ are as defined in compound of formula (I).

In another embodiment, the present invention provides a compound of formula (IA):
wherein,
$R_1$ represents hydrogen, —$CH_2$—COOH, —$CH_2$—$CONH_2$, —CH($CH_3$)—$CH_2$—$CH_3$, —$(CH_2)_2CONH_2$, —$(CH_2)_2COOH$, —$(CH_2)_3NH(C=NH)NH_2$, —$(CH_2)_4NH_2$, —$CH_2$-indolyl, —$CH_2$-imidazolyl or —$CH_2$-phenyl;
$R_b$ is hydrogen; $R_3$ represents hydrogen, —$CH_2$—COOH, —CH($CH_3$)—$CH_2$—$CH_3$, —$CH_2$—CH($CH_3$)$_2$, —$(CH_2)_4NH_2$, —$(CH_2)_2CONH_2$, —$(CH_2)_2COOH$, —$CH_2$-phenyl, $CH_2$-imidazolyl or $CH_2$-imidazolyl; or $R_b$ is hydrogen. In certain embodiments, in formula (IB), $R_b$ and $R_3$, together with the atoms to which they are attached form pyrrolidine ring.

In certain embodiments, $R_1$ represents hydrogen, —$CH_2$—COOH, —$CH_2$—$CONH_2$, —CH($CH_3$)—$CH_2$—$CH_3$, —$(CH_2)_2CONH_2$, —$(CH_2)_2COOH$, —$(CH_2)_3NH(C=NH)NH_2$, —$(CH_2)_4NH_2$, —$CH_2$-indolyl, —$CH_2$-imidazolyl or —$CH_2$-phenyl.

In certain embodiments, $R_1$ represents hydrogen, —$(CH_2)_2CONH_2$, —$(CH_2)_2COOH$, —$(CH_2)_3NH(C=NH)NH_2$, —$(CH_2)_4NH_2$, or —$CH_2$-phenyl.

In certain embodiments, $R_1$ represents —$(CH_2)_2CONH_2$, or —$(CH_2)_2COOH$.

In certain embodiments, $R_3$ represents hydrogen, —$CH_2$-phenyl, —$(CH_2)_2CONH_2$, or —$(CH_2)_2COOH$.

In certain embodiments, $R_b$ is hydrogen; $R_3$ represents hydrogen, —$CH_2$—COOH, —$CH_2$—CH($CH_3$)$_2$, —CH($CH_3$)—$CH_2$—$CH_3$, —$(CH_2)_4NH_2$, —$(CH_2)_2CONH_2$, —$(CH_2)_2COOH$, —$CH_2$-phenyl, $CH_2$-imidazolyl or $CH_2$-imidazolyl; or $R_b$ is hydrogen. In certain embodiments, in formula (IB), $R_b$ and $R_3$, together with the atoms to which they are attached form pyrrolidine ring.

In certain embodiments, $R_3$ represents hydrogen, or —$CH_2$-phenyl.

In certain embodiments, in formula (IB), $R_b$ is hydrogen. In certain embodiments, in formula (IB), $R_b$ and $R_3$, together with the atoms to which they are attached form pyrrolidine ring.

In certain embodiments, the present invention provides compound of formula (IB), wherein
$R_1$ represents —$(CH_2)_2CONH_2$, or —$(CH_2)_2COOH$; and
$R_b$ is hydrogen; and $R_3$ represents hydrogen, or —$CH_2$-phenyl; or $R_b$ and $R_3$, together with the atoms to which they are attached form pyrrolidine ring.

In certain embodiments, the compounds of formula (I) are,

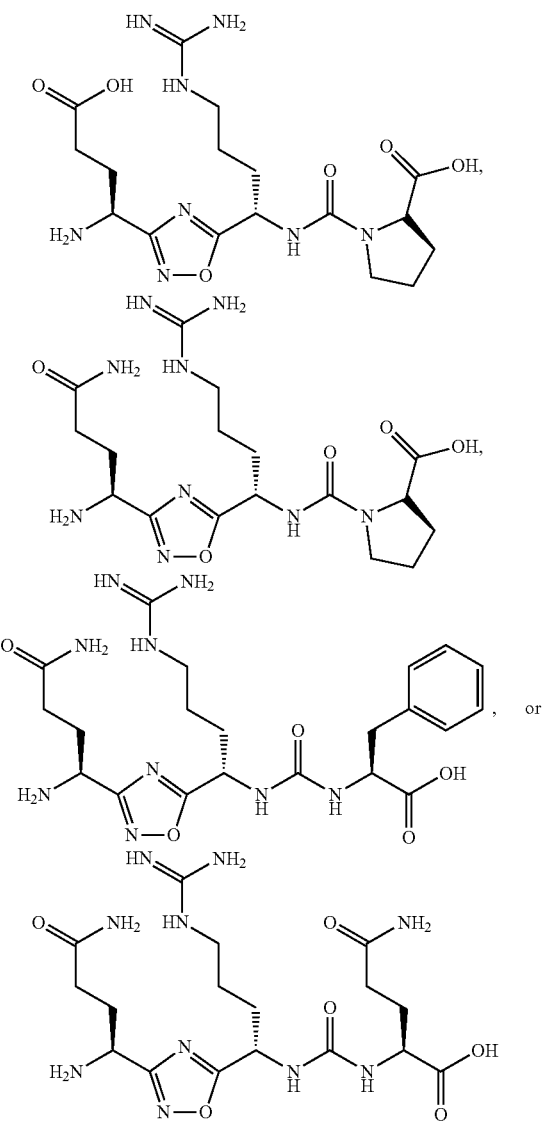

or a pharmaceutically acceptable salt or an amide or an ester, or a stereoisomer thereof.

In certain embodiments, the present invention provides a compound of formula (IC):

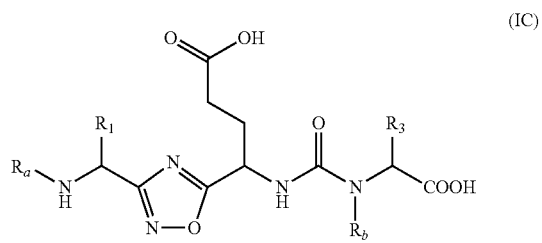

(IC)

or a pharmaceutically acceptable salt or an amide or an ester, or a stereoisomer thereof;

wherein, $R_1$, $R_a$, $R_3$ and $R_b$ are as defined in compound of formula (I).

In certain embodiments, $R_1$ represents —(CH$_2$)$_2$COOH, —(CH$_2$)$_2$CONH$_2$, (CH$_2$)$_3$NH(C=NH)NH$_2$, or —(CH$_2$)$_4$NH$_2$.

In certain embodiments, $R_1$ represents —(CH$_2$)$_2$CONH$_2$, —(CH$_2$)$_3$NH(C=NH)NH$_2$, or —(CH$_2$)$_4$NH$_2$.

In certain embodiments, $R_1$ represents —(CH$_2$)$_2$CONH$_2$, or —(CH$_2$)$_3$NH(C=NH)NH$_2$.

In certain embodiments, in formula (IC), $R_a$ is hydrogen.

In certain embodiments, in formula (IC), $R_a$ and $R_1$, together with the atoms to which they are attached form pyrrolidine ring.

In certain embodiments, $R_3$ represents hydrogen, —CH$_2$-phenyl, —(CH$_2$)$_3$NHC(=NH)NH$_2$, —CH$_2$-imidazolyl or $R_b$ and $R_3$, together with the atoms to which they are attached form pyrrolidine ring.

In certain embodiments, $R_3$ represents hydrogen, —CH$_2$-phenyl, —(CH$_2$)$_3$NHC(=NH)NH$_2$, or —CH$_2$-imidazolyl.

In certain embodiments, in formula (IC), $R_b$ is hydrogen. In certain embodiments, in formula (IC), $R_b$ and $R_3$, together with the atoms to which they are attached form pyrrolidine ring.

In another embodiments, the present invention provides a compound of formula (IC):
wherein
$R_1$ represents —(CH$_2$)$_2$COOH, —(CH$_2$)$_2$CONH$_2$, —(CH$_2$)$_3$NH(C=NH)NH$_2$, or —(CH$_2$)$_4$NH$_2$; and
$R_3$ represents hydrogen, —CH$_2$-phenyl, —(CH$_2$)$_2$CONH$_2$, or —(CH$_2$)$_2$COOH.

In another embodiment, the present invention provides a compound of formula (IC):
wherein
$R_a$ is hydrogen; and $R_1$ represents —(CH$_2$)$_2$CONH$_2$, —(CH$_2$)$_3$NH(C=NH)NH$_2$, or —(CH$_2$)$_4$NH$_2$, or $R_a$ and $R_1$, together with the atoms to which they are attached form pyrrolidine ring; and
$R_b$ is hydrogen; and $R_3$ represents —CH$_2$-phenyl, —(CH$_2$)$_3$NHC(=NH)NH$_2$, or —CH$_2$— imidazolyl; or $R_b$ and $R_3$, together with the atoms to which they are attached form pyrrolidine ring.

In another embodiments, the present invention provides a compound of formula (IC):
wherein
$R_a$ is hydrogen; and $R_1$ represents —(CH$_2$)$_2$CONH$_2$, or —(CH$_2$)$_3$NH(C=NH)NH$_2$, or $R_a$ and $R_1$, together with the atoms to which they are attached form pyrrolidine ring; and
$R_b$ is hydrogen; and $R_3$ represents hydrogen, —CH$_2$-phenyl, —(CH$_2$)$_3$NHC(=NH)NH$_2$, or —CH$_2$-imidazolyl; or $R_b$ and $R_3$, together with the atoms to which they are attached form pyrrolidine ring.

In certain embodiments, the compounds of formula (I) are:

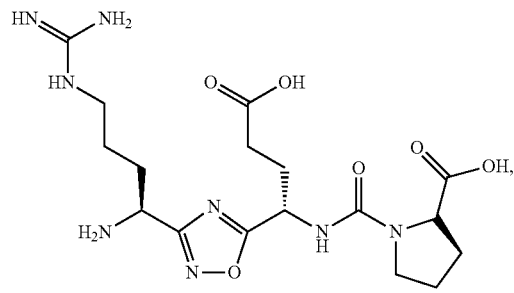

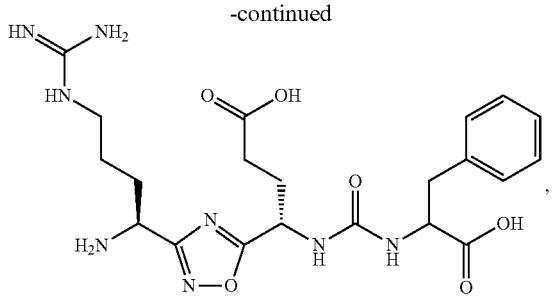

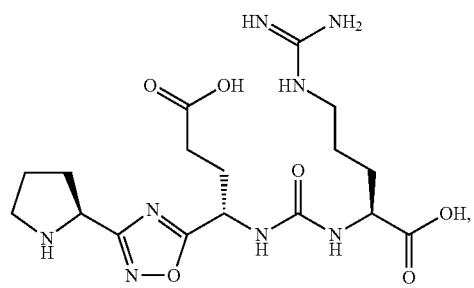

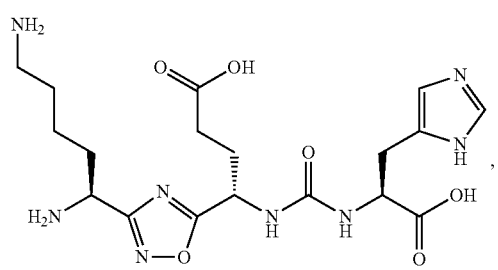

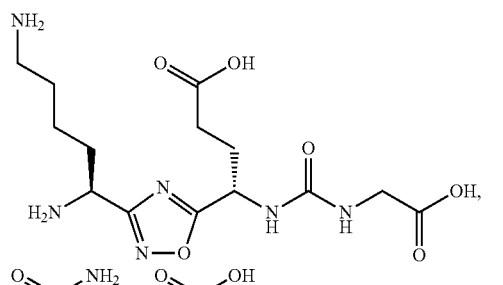

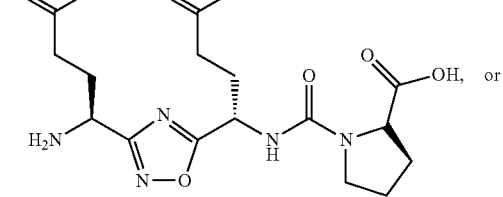

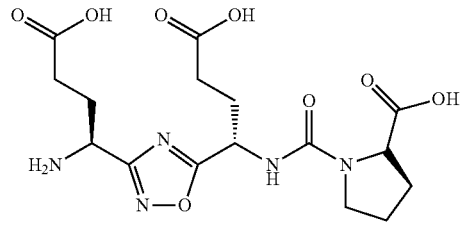

or a pharmaceutically acceptable salt or an amide or an ester, or a stereoisomer thereof.

In certain embodiments, the present invention provides a compound of formula (ID):

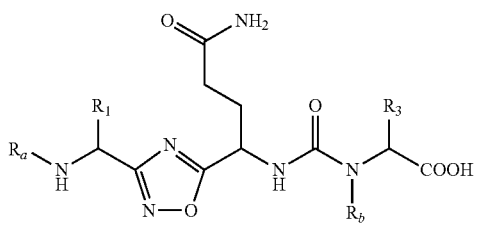

(ID)

or a pharmaceutically acceptable salt or an amide or an ester, or a stereoisomer thereof;

wherein, $R_1$, $R_a$, $R_3$ and $R_b$ are as defined in compound of formula (I).

In certain embodiments, $R_1$ represents —$(CH_2)_3$NH(C=NH)$NH_2$, —$(CH_2)_4NH_2$, or —$CH_2CONH_2$.

In certain embodiments, $R_3$ represents hydrogen, —$(CH_2)_3$NHC(=NH)$NH_2$, or —$(CH_2)_4NH_2$.

In certain embodiments, in formula (ID), $R_b$ is hydrogen. In certain embodiments, in formula (ID), $R_b$ and $R_3$, together with the atoms to which they are attached form pyrrolidine ring.

In certain embodiments, wherein $R_b$ is hydrogen; $R_3$ represents hydrogen, —$(CH_2)_3$NHC(=NH)$NH_2$, or —$(CH_2)_4NH_2$, or $R_b$ and $R_3$, together with the atoms to which they are attached form pyrrolidine ring.

In another embodiment, the present invention provides a compound of formula (ID): wherein $R_1$ represents —$(CH_2)_3$NH(C=NH)$NH_2$, —$(CH_2)_4NH_2$, or —$CH_2CONH_2$; and $R_b$ is hydrogen; $R_3$ represents hydrogen, —$(CH_2)_3$NHC(=NH)$NH_2$, or —$(CH_2)_4NH_2$, or $R_b$ and $R_3$, together with the atoms to which they are attached form a pyrrolidine ring In another embodiment, the present invention provides a compound of formula (ID):
wherein $R_1$ represents —$(CH_2)_3$NH(C=NH)$NH_2$, —$(CH_2)_4NH_2$, or —$CH_2CONH_2$;

$R_b$ is hydrogen; and $R_3$ represents hydrogen, —$(CH_2)_3$NHC(=NH)$NH_2$, or —$(CH_2)_4NH_2$; or $R_b$ and $R_3$, together with the atoms to which they are attached form pyrrolidine ring.

In certain embodiments, the compounds of formula (I) are:

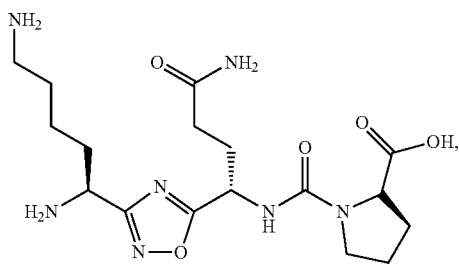

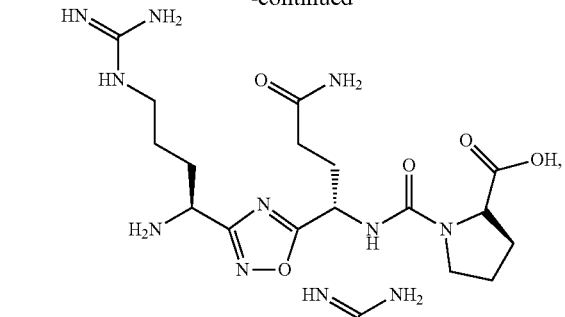

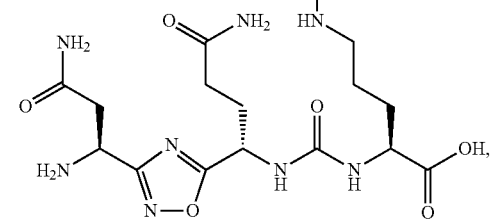

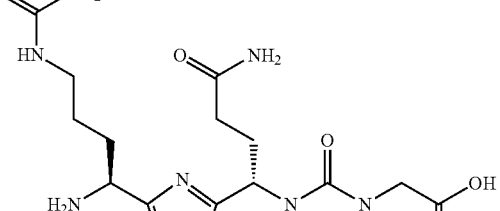

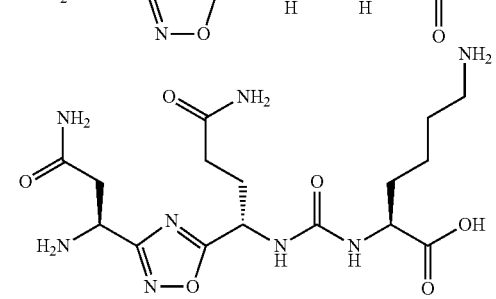

or a pharmaceutically acceptable salt or an amide or an ester, or a stereoisomer thereof.

In certain embodiments, the present invention provides a compound of formula (IE):

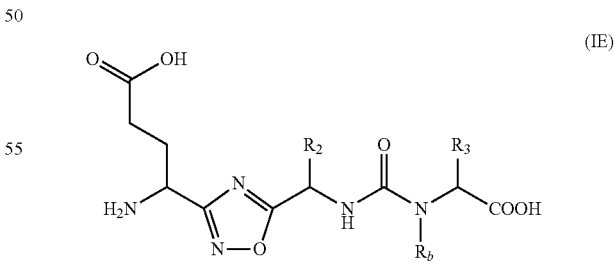

(IE)

or a pharmaceutically acceptable salt or an amide or an ester, or a stereoisomer thereof wherein, $R_2$, $R_3$ and $R_b$ are as defined in compound of formula (I).

In certain embodiments, $R_2$ represents hydrogen, —$CH_2$—OH, —$(CH_2)_2$COOH, —$(CH_2)_3$NHC(=NH)$NH_2$, —$CH_2$-phenyl or —$CH_2$— indolyl.

In certain embodiments, $R_2$ represents hydrogen, or —$(CH_2)_3NHC(=NH)NH_2$.

In another embodiment, the present invention provides a compound of formula (IE):
wherein;
$R_2$ represents hydrogen, —$CH_2$—OH, —$(CH_2)_2COOH$, —$(CH_2)_3NHC(=NH)NH_2$, —$CH_2$-phenyl or —$CH_2$-indol; and
$R_3$ represents hydrogen, —$CH_2$—COOH, —$(CH_2)_2COOH$, —$CH_2$—$CH(CH_3)_2$, —$CH(CH_3)$—$CH_2$—$CH_3$, —$(CH_2)_4NH_2$, —$CH_2$-phenyl, —$CH_2$-indolyl, or —$CH_2$— imidazolyl or $R_b$ and $R_3$, together with the atoms to which they are attached form pyrrolidine ring.

In certain embodiments, in formula (IE), $R_b$ and $R_3$, together with the atoms to which they are attached form a pyrrolidine ring.

In certain embodiments, $R_2$ represents hydrogen, —$(CH_2)_3NHC(=NH)NH_2$, —$CH_2$—OH—$(CH_2)_2COOH$, —$CH_2$-phenyl or —$CH_2$-indolyl.

In another embodiments, the present invention provides a compound of formula (IE): wherein,
$R_2$ represents hydrogen, or —$(CH_2)_3NHC(=NH)NH_2$; $R_b$ and $R_3$, together with the atoms to which they are attached form pyrrolidine ring.

In certain embodiments, $R_3$ represents hydrogen, —$CH_2$—COOH, —$(CH_2)_2COOH$, —$CH_2$—$CH(CH_3)_2$, —$CH(CH_3)$—$CH_2$—$CH_3$, —$(CH_2)_4NH_2$, —$CH_2$-phenyl, —$CH_2$-indolyl, or —$CH_2$— imidazolyl or $R_b$ and $R_3$, together with the atoms to which they are attached form pyrrolidine ring;

In certain embodiments, the present invention provides a compound of formula (IF):

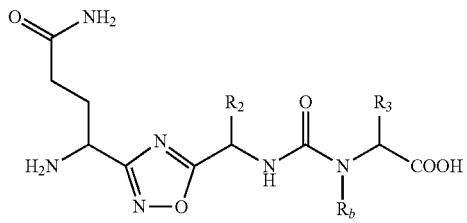

(IF)

or a pharmaceutically acceptable salt or an amide or an ester, or a stereoisomer thereof;
wherein, $R_2$, $R_3$ and $R_b$ are as defined in compound of formula (I).

In certain embodiments, $R_2$ represents hydrogen, —$CH_2$-phenyl, —$(CH_2)_3NHC(=NH)NH_2$, or —$(CH_2)_2COOH$.

In certain embodiments, $R_3$ represents —$CH_2$-phenyl, —$(CH_2)_2CONH_2$, —$(CH_2)_2COOH$, or —$(CH_2)_4NH_2$.

In certain embodiments, $R_3$ represents —$CH_2$-phenyl, —$(CH_2)_2CONH_2$, or —$(CH_2)_2COOH$.

In certain embodiments, in formula (IF), $R_b$ is hydrogen. In certain embodiments, in formula (IF), $R_b$ and $R_3$, together with the atoms to which they are attached form pyrrolidine ring.

In certain embodiments, the present invention provides a compound of formula (IF),
wherein
$R_2$ represents hydrogen, —$CH_2$-phenyl, —$(CH_2)_3NHC(=NH)NH_2$, or —$(CH_2)_2COOH$; and
$R_3$ represents —$CH_2$-phenyl, —$(CH_2)_2CONH_2$, —$(CH_2)_2COOH$, or —$(CH_2)_4NH_2$.

In certain embodiments, the present invention provides a compound of formula (IF):
wherein
$R_2$ represents hydrogen, —$CH_2$-phenyl, —$(CH_2)_3NHC(=NH)NH_2$, or —$(CH_2)_2COOH$;
$R_b$ is hydrogen; and $R_3$ represents —$CH_2$-phenyl, —$(CH_2)_2CONH_2$, or —$(CH_2)_2COOH$; or $R_b$ and $R_3$, together with the atoms to which they are attached form pyrrolidine ring.

In certain embodiments, the compounds of formula (I) are:

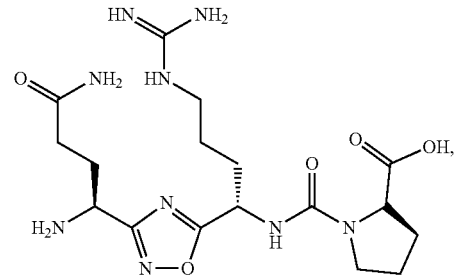

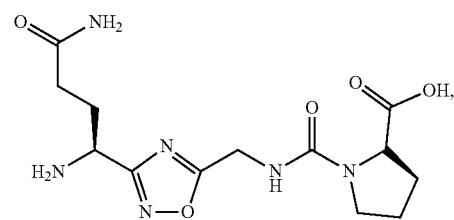

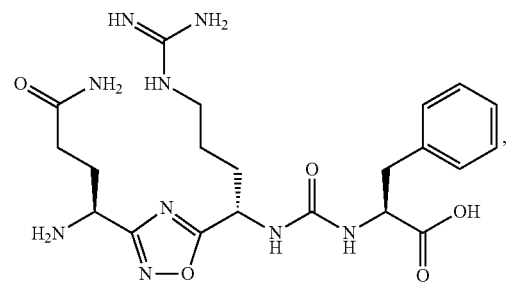

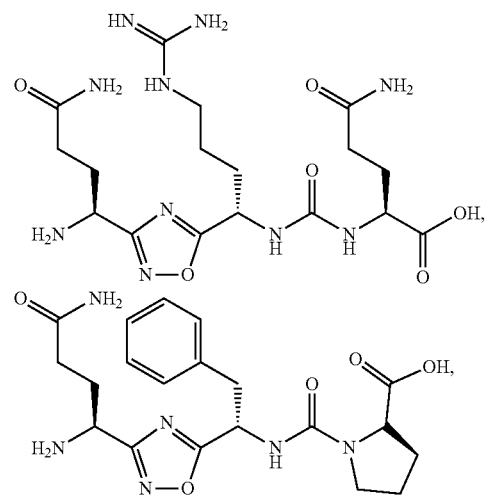

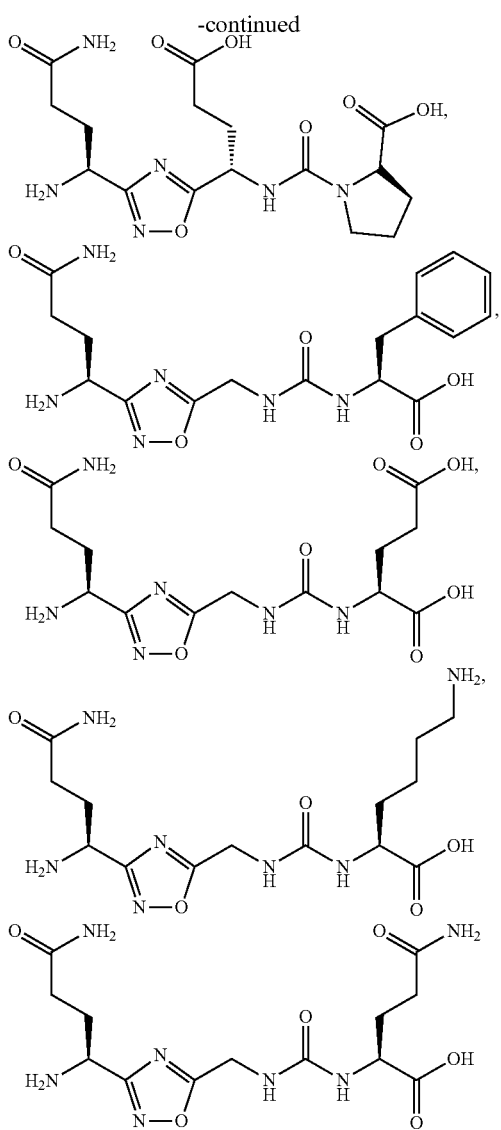

or a pharmaceutically acceptable salt or an amide or an ester, or a stereoisomer thereof.

In certain embodiments, $R_a$ is hydrogen; and $R_1$ represents hydrogen, —$(CH_2)_2CONH_2$, —$(CH_2)_2COOH$, —$(CH_2)_3NHC(=NH)NH_2$, —$(CH_2)_4NH_2$, —$CH_2CONH_2$, —$CH_2$-aryl, or —$CH_2$-heteroaryl; or $R_a$ and $R_1$, together with the atoms to which they are attached form pyrrolidine ring;

$R_2$ represents hydrogen, —$(CH_2)_3NHC(=NH)NH_2$, —$(CH_2)_2CONH_2$, —$(CH_2)_2COOH$, —$CH_2$-aryl, or —$CH_2$-heteroaryl;

$R_b$ is hydrogen; and $R_3$ represents hydrogen, —$CH_2$-aryl, —$(CH_2)_3NHC(=NH)NH_2$, —$(CH_2)_2CONH_2$, —$(CH_2)_2COOH$, —$(CH_2)_4NH_2$ or —$CH_2$-heteroaryl; or $R_b$ and $R_3$, together with the atoms to which they are attached form pyrrolidine ring.

In certain embodiments, $R_a$ is hydrogen; and $R_1$ represents hydrogen, —$(CH_2)_2CONH_2$, —$(CH_2)_2COOH$, —$(CH_2)_3NHC(=NH)NH_2$, —$(CH_2)_4NH_2$, —$CH_2CONH_2$, —$CH_2$-phenyl, or —$CH_2$-imidazolyl; or $R_a$ and $R_1$, together with the atoms to which they are attached form pyrrolidine ring;

$R_2$ represents hydrogen, —$(CH_2)_3NHC(=NH)NH_2$, —$(CH_2)_2CONH_2$, —$(CH_2)_2COOH$, —$CH_2$—phenyl, or —$CH_2$-imidazolyl;

$R_b$ is hydrogen; and $R_3$ represents hydrogen, —$CH_2$-phenyl, —$(CH_2)_3NHC(=NH)NH_2$, —$(CH_2)_2CONH_2$, —$(CH_2)_2COOH$, —$(CH_2)_4NH_2$ or —$CH_2$-imidazolyl; or $R_b$ and $R_3$, together with the atoms to which they are attached form pyrrolidine ring.

In certain embodiments, the present invention provides a compound that is:

| Compound | Structure |
|---|---|
| 1 | 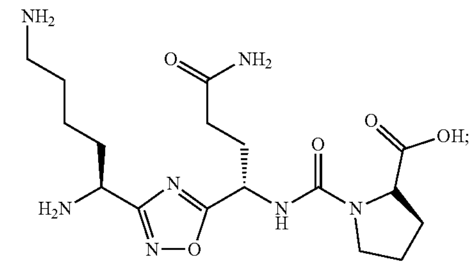 |
| 2 | 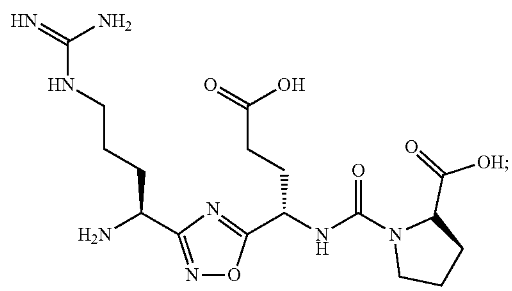 |
| 3 | 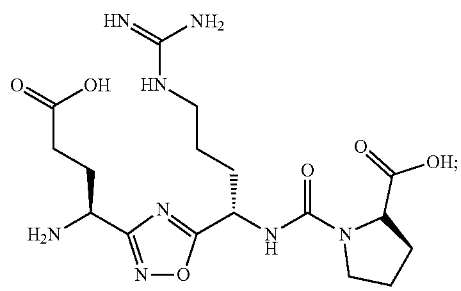 |
| 4 | 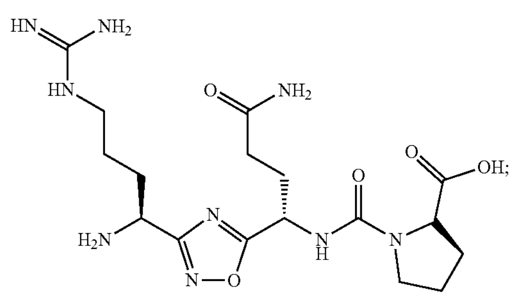 |

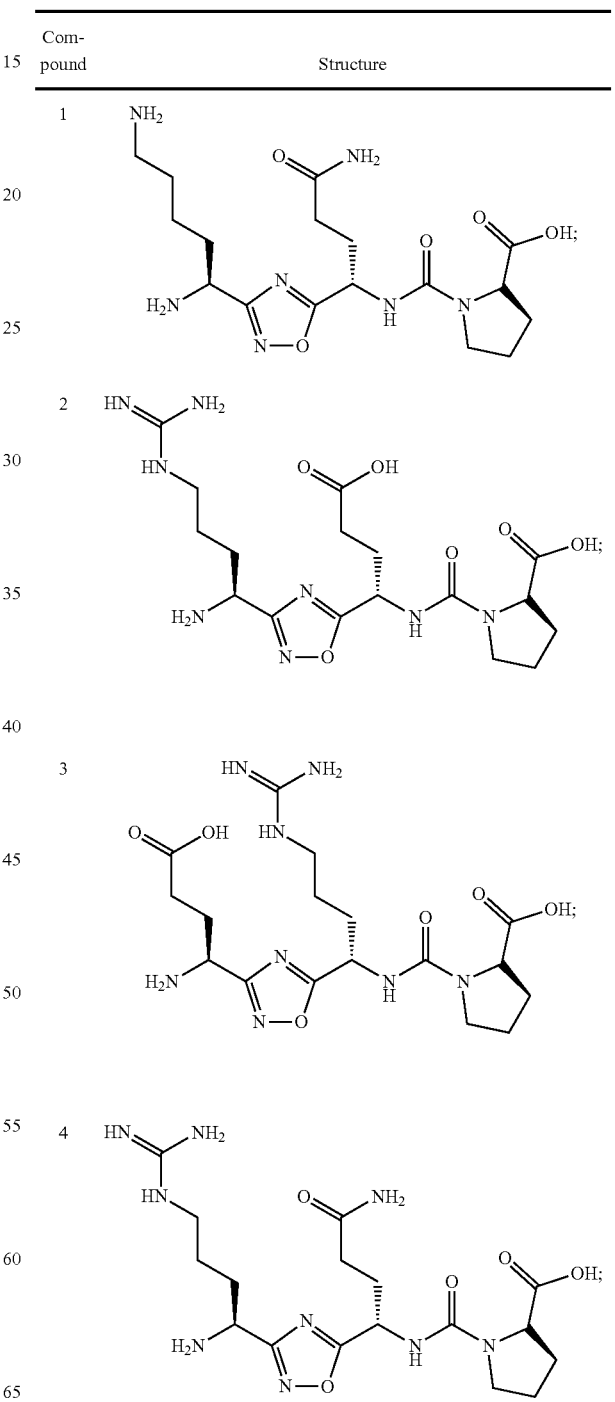

-continued
| Compound | Structure |
|---|---|
| 5 | 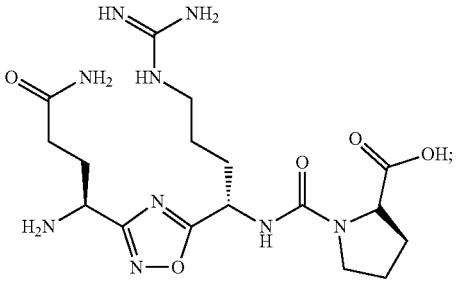 |
| 6 | 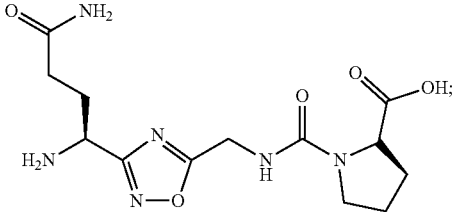 |
| 7 | 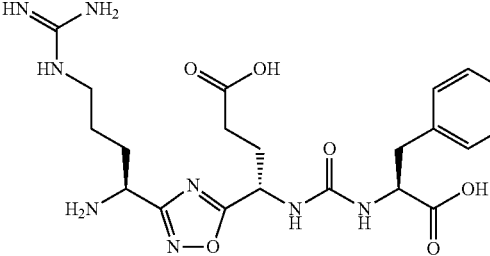 |
| 8 | 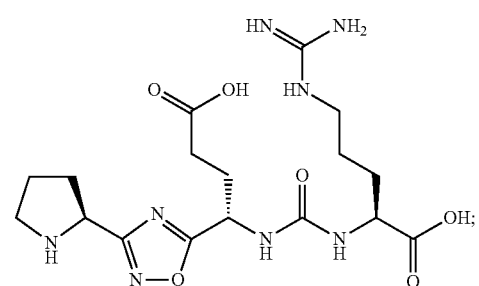 [SMILES: N=C(N)NCCC[C@H](NC(=O)N[C@@H](CCC(=O)O)c1nc([C@@H]2CCCN2)no1)C(=O)O] |
| 9 | 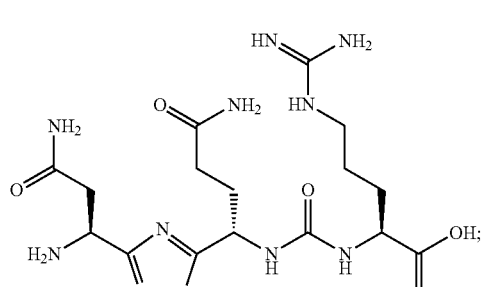 |
| 10 | 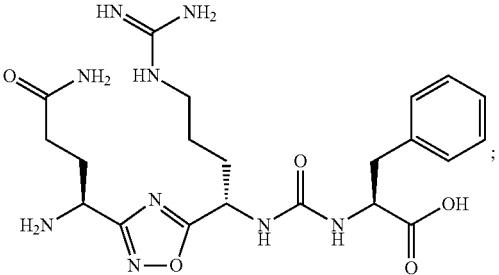 [SMILES: N=C(N)NCCC[C@H](NC(=O)N[C@@H](Cc1ccccc1)C(=O)O)c1nc([C@@H](N)CCC(N)=O)no1] |
| 11 | 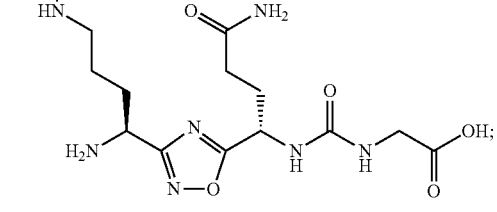 |
| 12 | 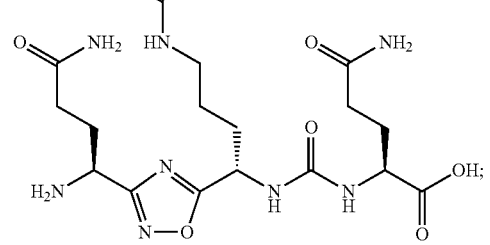 |
| 13 | 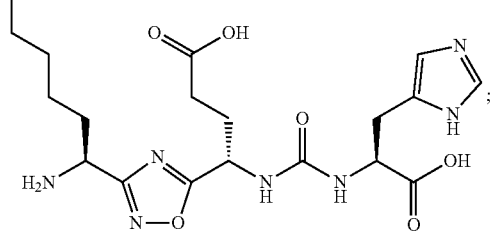 |
| 14 | 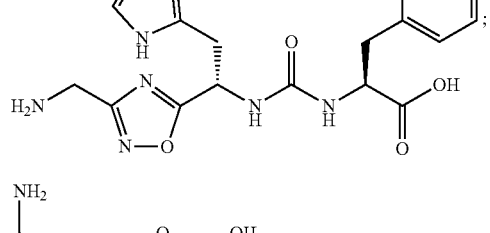 |
| 15 | 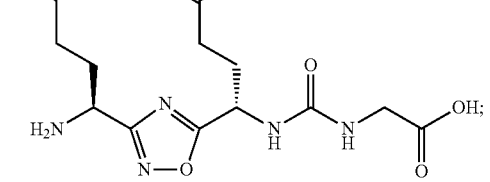 |

| Compound | Structure |
|---|---|
| 16 | 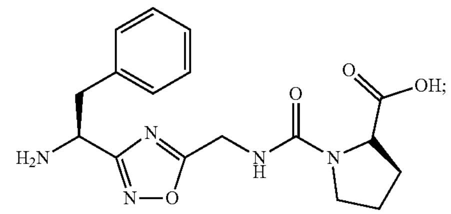 |
| 17 | 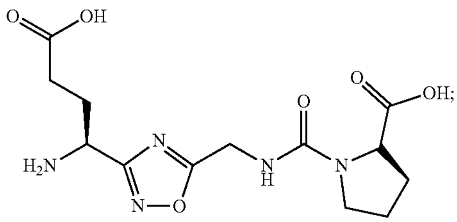 |
| 18 | 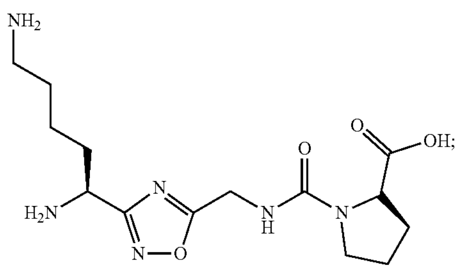 |
| 19 | 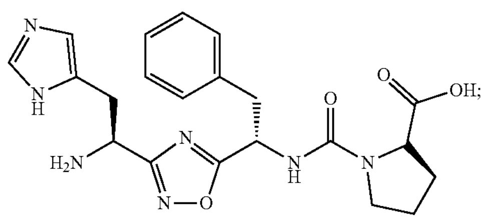 |
| 20 | 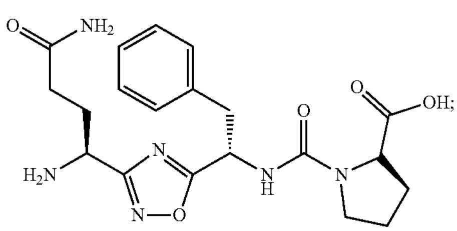 |
| 21 | 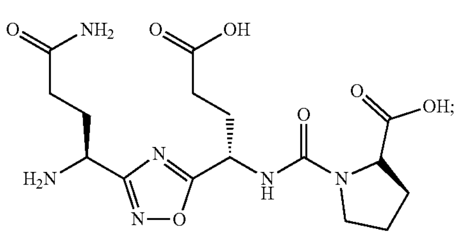 |
| 22 | 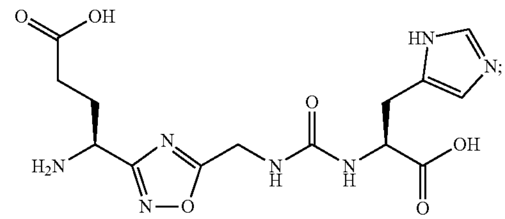 [SMILES: N[C@@H](CCC(=O)O)c1noc(CNC(=O)N[C@@H](Cc2cnc[nH]2)C(=O)O)n1] |
| 23 | 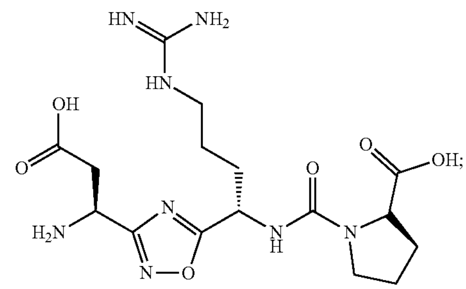 |
| 24 | 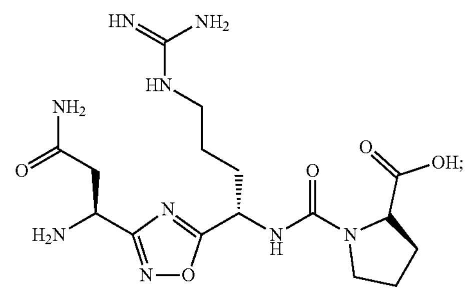 |
| 25 | 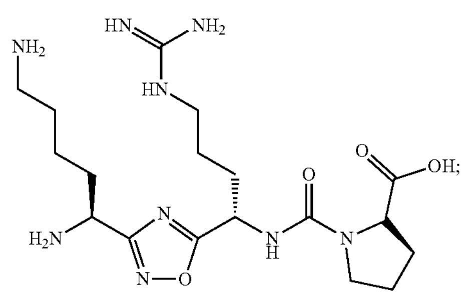 |
| 26 | 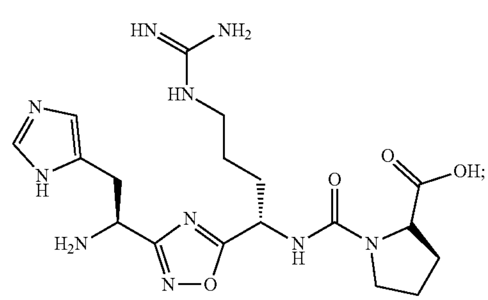 |

| Compound | Structure |
|---|---|
| 27 | *(structure)* |
| 28 | *(structure)* |
| 29 | *(structure)* |
| 30 | *(structure)* |
| 31 | *(structure)* |
| 32 | *(structure)* |
| 33 | *(structure)* |
| 34 | *(structure)* |
| 35 | *(structure)* |
| 36 | *(structure)* |

-continued

| Compound | Structure |
|---|---|
| 37 | (structure) |
| 38 | (structure) |
| 39 | (structure) |
| 40 | (structure) |
| 41 | (structure) |

-continued

| Compound | Structure |
|---|---|
| 42 | (structure) |
| 43 | (structure) |
| 44 | (structure) |
| 45 | (structure) |
| 46 | (structure) |

| Compound | Structure |
|---|---|
| 47 | (structure) |
| 48 | (structure) |
| 49 | (structure) |
| 50 | (structure) |
| 51 | (structure) |
| 52 | (structure) |
| 53 | (structure) |
| 54 | (structure) | or a pharmaceutically acceptable salt or an amide or an ester, or a stereoisomer thereof.

In certain embodiments, the present invention provides a compound that is:

| Compound | Structure |
|---|---|
| 2 | (structure) |
| 3 | (structure) |

US 11,274,123 B2
35
-continued
| Compound | Structure |
|---|---|
| 5 | 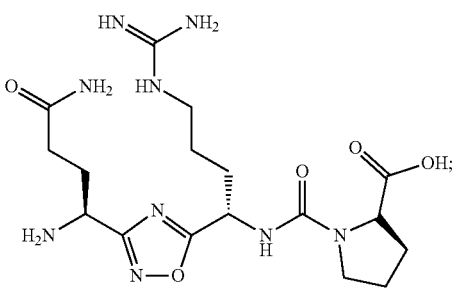 |
| 6 | 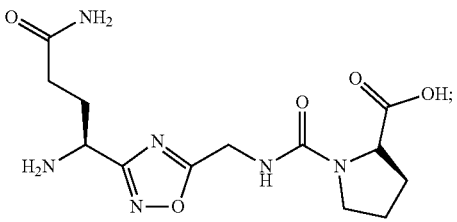 |
| 7 | 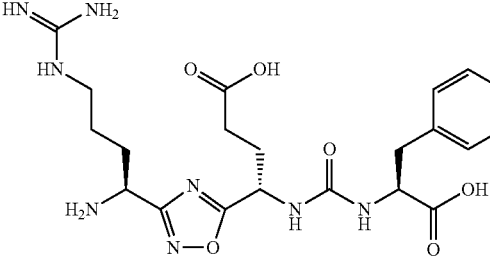 |
| 8 | 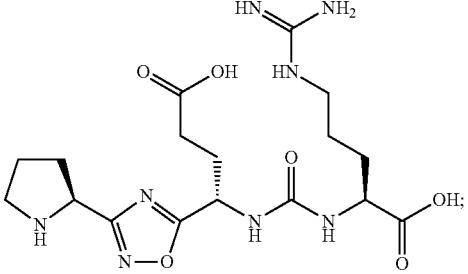 [SMILES: N=C(N)NCCC[C@H](NC(=O)N[C@@H](CCC(=O)O)c1nc([C@@H]2CCCN2)no1)C(=O)O] |
| 10 | 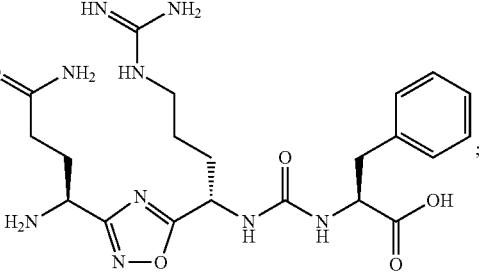 |
36
-continued
| Compound | Structure |
|---|---|
| 12 | 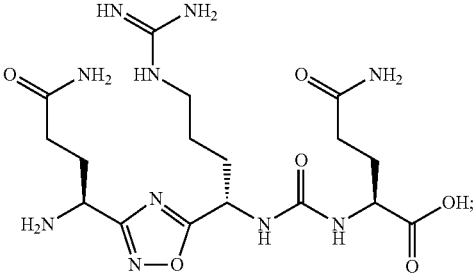 [SMILES: N=C(N)NCCC[C@H](NC(=O)N[C@@H](CCC(N)=O)C(=O)O)c1nc([C@@H](N)CCC(N)=O)no1] |
| 14 | 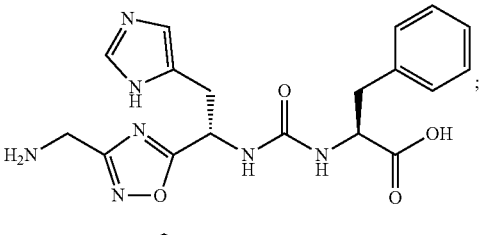 |
| 16 | 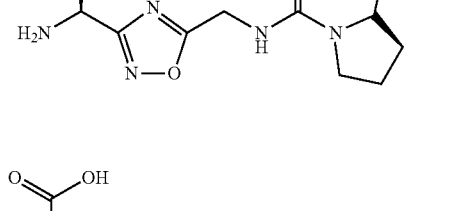 |
| 17 | 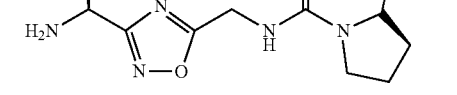 |
| 18 | 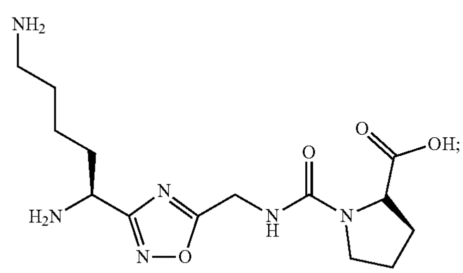 |
| 21 | 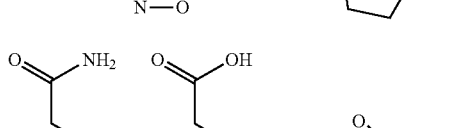 |

| Compound | Structure |
|---|---|
| 41 | [structure] |
| 42 | [structure] |
| 43 | [structure] |
| 49 | [structure] |
| 50 | [structure] | or a pharmaceutically acceptable salt or an amide or an ester, or a stereoisomer thereof.

In certain embodiments, the present invention provides a pharmaceutical composition comprising compounds as disclosed herein, optionally admixed with a pharmaceutically acceptable carrier or diluent.

The present invention also provides methods for formulating the disclosed compounds for pharmaceutical administration.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound of present invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution;

(19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the present the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the compounds described herein enhance macrophage phagocytic activity towards a cancer cell, e.g., an AML cell. In other embodiments, the phagocytic activity is enhanced, e.g., 1%, 5%, 10%, 20%, 30%, 40%, 50%, 60%, 70%, 80%, or 90%, relative to a macrophage in the absence of the compounds described herein.

In certain embodiments, the present invention provides uses of compounds of the present invention for the preparation of a medicament.

In certain embodiments, the present invention provides uses of compounds of the present invention for the preparation of a medicament, e.g., for the treatment of cancer.

In certain embodiments, the present invention provides methods for treating cancer, wherein the method comprises administration of compounds of the present invention, e.g., in a therapeutically effective amount, to the subject in need thereof.

In certain embodiments, the present invention provides methods for inhibiting growth of tumour cells and/or metastasis by administering a compound of the present invention, e.g., in a therapeutically effective amount, to the subject in need thereof.

In certain embodiments, the present invention provides the compound of formula (I), or a pharmaceutically acceptable salt or an amide or an ester, or a stereoisomer thereof, for the treatment of cancer, wherein, $R_a$ is hydrogen; and $R_1$ represents hydrogen, —$(CH_2)_2CONH_2$, —$(CH_2)_2COOH$, —$CH_2COOH$, —$(CH_2)_3NH(C=NH)NH_2$, —$(CH_2)_4NH_2$, —$CH_2CONH_2$, —$CH(CH_3)$—$CH_2$—$CH_3$, —$CH_2$-aryl, or —$CH_2$— heteroaryl; wherein the said aryl and heteroaryl are unsubstituted; or $R_a$ and $R_1$, together with the atoms to which they are attached form pyrrolidine ring optionally substituted with oxo group;

$R_2$ represents hydrogen, —$CH_2$—OH, —$(CH_2)_3NHC(=NH)NH_2$, —$(CH_2)_2CONH_2$, —$(CH_2)_2COOH$, —$CH_2$-aryl, or —$CH_2$-heteroaryl; wherein the said aryl and heteroaryl are unsubstituted;

$R_b$ is hydrogen; and $R_3$ represents hydrogen, —$CH_2$-aryl, —$(CH_2)_3NHC(=NH)NH_2$, —$CH_2COOH$, —$CH(CH_3)$—$CH_2$—$CH_3$, —$CH_2$—$CH(CH_3)_2$, —$(CH_2)_2CONH_2$, —$(CH_2)_2COOH$, —$(CH_2)_4NH_2$ or —$CH_2$-heteroaryl; wherein the said aryl and heteroaryl are unsubstituted; or $R_b$ and $R_3$, together with the atoms to which they are attached form pyrrolidine ring.

Representative tumor cells include cells of a cancer such as, but not limited to, melanoma, renal cancer, prostate cancer, breast cancer, colon cancer and lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), non-small cell lung cancer (NSCLC), primary CNS lymphoma, tumour angiogenesis, spinal axis tumour, brain stem glioma, pituitary adenoma, Kaposi's sarcoma, epidermoid cancer, squamous cell cancer, T-cell lymphoma, B-cell lymphomas, environmentally induced cancers including those induced by asbestos (e.g., mesothelioma), and combinations of said cancers.

In certain embodiments, the present invention provides uses of compounds of the present invention for the preparation of a medicament for the treatment of bacterial, viral and fungal infection, as well as methods of administering a compounds of the present invention, e.g., in a therapeutically effective amount, for the treatment of a bacterial, viral, or fungal infection.

Still yet other embodiments of the present invention provide a methods of treatment of infection by blockade of the CD-47 pathway comprising administering a compound of the present invention to the subject in need thereof, e.g., in a therapeutically effective amount.

In certain embodiments, the invention provides uses of compounds of the present invention in inhibiting the CD-47 pathway.

In certain embodiments, the present invention provides methods for treating infectious disease in a subject comprising administering a compound of the present invention, e.g., in a therapeutically effective amount, for the treatment of the infectious disease.

Representative infectious disease include, but are not limited to, HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, or *Nippostrongylus brasiliensis*.

In certain embodiments, the present invention provides method for treating or delaying progression of atherosclerosis and multiple sclerosis mediated by CD47 in an individual, the method comprising administering to the said individual an effective amount of a compound of formula (I).

In certain embodiments, the present invention provides methods for the treatment of atherosclerosis and multiple sclerosis in a subject comprising administering a therapeutically effective amount of compound of formula (I).

The compounds may be used by themselves, or, preferably, in a pharmaceutical composition in which the compound is mixed with one or more pharmaceutically acceptable materials.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, the term 'compound(s)' comprises the compounds of formula (I), (IA), (IB), (IC), (ID), (IE), (IF) and their pharmaceutically acceptable salts or stereoisomers thereof.

The term "aryl" as used herein includes, unless otherwise specified, substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls and/or heterocyclyls. Aryl groups include benzene, naphthalene, phenanthrene, and the like. Preferably the term 'aryl' includes phenyl.

The term "heteroaryl" includes, unless otherwise specified, substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls and/or heterocyclyls. Heteroaryl groups include, for example, pyrrole, furan, thiophene, imidazole, oxazole, thiazole, pyrazole, pyridine, pyrazine, pyridazine, indole, 1,2,4-oxadiazole, 1,3,4-oxadiazole, 1,3,4-thiadiazole, benzimidazole, pyrimidine and the like. A heteroaryl group may be substituted at one or more positions, as permitted by valence, with any optional substituents described herein. Preferably the term 'heteroaryl' includes imidazolyl, and indolyl.

The term "acyl" is art-recognized and refers to a group represented by the general formula alkyl-C(O)—. The examples of the 'acyl' group are, but not limited to, acetyl, propionyl and butyryl.

As used herein, a therapeutic that "prevents" a disorder or condition refers to a compound that, in a statistical sample, reduces the occurrence of the disorder or condition in the treated sample relative to an untreated control sample or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate or stabilize the existing unwanted condition or side effects thereof).

As used herein, the phrase "delaying progression" refers to the procedures or applications that are intended to delay in time the development of a disease or symptoms of a disease (including delaying in time the appearance or occurrence of at least one symptom of the particular disease).

The term "prodrug" is intended to encompass compounds which, under physiologic conditions, are converted into the therapeutically active agents of the present invention (e.g., a compound of formula (I)). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula (I) in a formulation represented above can be replaced with the corresponding suitable prodrug, e.g., wherein a hydroxyl in the parent compound is presented as an ester or a carbonate or carboxylic acid present in the parent compound is presented as an ester.

As used herein, the term "comprise" or "comprising" is generally used in the sense of include, that is to say permitting the presence of one or more additional (unspecified) features or components.

As used herein, the term "including" as well as other forms, such as "include", "includes," and "included," is not limiting.

As used herein, the term "disease" or "disorder" refers to a pathological condition in an organism resulting from cause or condition including, but not limited to, infections, acquired conditions, genetic conditions, and characterized by identifiable symptoms. Diseases and disorders also include those that are caused by the absence of a compound, such as TIGIT modulators.

As used herein, "patient" or "subject" or "individual" to be treated includes humans and or non-human animals, including mammals. Mammals include primates, such as humans, chimpanzees, gorillas and monkeys; domesticated animals, such as dogs, horses, cats, pigs, goats, cows; and rodents such as mice, rats, hamsters and gerbils.

This invention includes pharmaceutically acceptable salts of compounds of the invention and their use in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

As used herein, the term "pharmaceutically acceptable salt" is intended to include all salts known and used in the art of pharmaceuticals. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzyl-phenethylamine, 1-para-chloro-benzyl-2-pyrrolidin-1'-ylmethyl-benzimidazole, diethylamine and other alkylamines, piperazine and tris(hydroxy-methyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Exemplary pharmaceutically acceptable salts include acetate, lactobionate, benzenesulfonate, laurate, benzoate, malate, bicarbonate, maleate, bisulfate, mandelate, bitartrate, mesylate, borate, methylbromide, methylnitrate, calcium edetate, methylsulfate, camsylate, mucate, carbonate, napsylate, bromide, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, triethiodide, lactate, panoate and valerate, which can be used as a dosage form for modifying the solubility or hydrolysis characteristics or can be used in sustained release or pro-drug formulations. The preparation of the pharmaceutically acceptable salts described above and other typical pharmaceutically acceptable salts is more fully described by Berg et al., "Pharmaceutical Salts," J. Pharm. Sci. 66: 1-19 (1977).

In certain preferred embodiments, this invention includes pharmaceutically acceptable salts of compounds of the invention and their use in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide and the like. Mixtures of such solvates can also be prepared. The source of such solvate can be from the solvent of crystallization, inherent in the solvent of preparation or crystallization or adventitious to such solvent.

The term "stereoisomers" refers to any enantiomers, diastereoisomers, or geometrical isomers, such as of the compounds of the invention. When compounds of the invention are chiral, they can exist in racemic or in optically active form. Since the pharmaceutical activity of the racemates or stereoisomers of the compounds according to the invention may differ, it may be desirable to use compounds that are enriched in one of the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

The term "ester", as used herein, refers to a group —C(O)OR$_{11}$ wherein R$_{11}$ represents a hydrocarbyl group.

The term "amide", as used herein, refers to a group —C(O)NH$_2$.

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de or even 95% or greater de.

The term "subject" includes mammals (especially humans) and other animals, such as domestic animals (e.g., household pets including cats and dogs) and non-domestic animals (such as wildlife).

The abbreviations used in the entire specification may be summarized herein below with their particular meaning:

° C. (degree Celsius); % (percentage); ACN (Acetonitrile), brine (NaCl solution); CH$_2$Cl$_2$/DCM (Dichloromethane); Boc (Tert-butyloxycarbonyl); DIC: N,N'-Diisopropylcarbodiimide; DMF (Dimethyl formamide); EtOH (Ethanol); Et$_2$NH (Diethylamine); ECF (Ethyl chloro formate), Fmoc (9-Fluorenylmethyloxycarbonyl); g or gr (gram); h or hr (Hours); HPLC (High-performance liquid chromatography); K$_2$CO$_3$ (Potassium carbonate); LCMS (Liquid chromatography mass spectroscopy); mmol (Millimoles); M (Molar); µl (Microlitre); mL (Millilitre); mg (Milligram); min (Minutes); NaHCO$_3$ (Sodium bicarbonate); NMM (N-Methylmorpholine); Na$_2$SO$_4$. (Sodium sulphate); NH$_3$ (Ammonia), NH$_2$OH. HCl (Hydroxylamine hydrochloride), prep-HPLC/preparative HOBt (Hydroxybenzotriazole); HPLC (Preparative High-performance liquid chromatography);

TEA/Et$_3$N (Triethylamine); THF (Tetrahydrofuran); TFA (Trifluoroacetic acid); TFAA (Trifluoro acetic acid anhydride), TIPS (Triisopropylsilane); t$_R$ (Retention time).

EXPERIMENTAL METHODS

The present invention provides methods for the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The intermediates or starting materials required for the synthesis are commercially available (commercial sources such as Sigma-Aldrich, USA or Germany; Chem-Impex USA; G.L. Biochem, China and Spectrochem, India) or alternatively, these intermediates or starting materials can be prepared using known literature methods. The invention is described in greater detail by way of specific examples.

Analytical HPLC methods
Method-1:
  Column: ZIC-HILLIC (Sequent), C18 (4.6×250 mm, 5 µm) 200 A°,
  Flow: 1.0 mL/min; Column Temp: 25.0° C.,
  Mobile phase: A=5 mM Ammonium Acetate PH-4.0 (Acetic Acid), IACN,
  Gradient (Time/% B): 0/85, 2/85, 20/40, 20.1/85, 30/85.
Method 2:
  Column: Phenomenex Aeris peptide C18 (2) 100 A (250× 4.6 mm, 3.6p),
  Flow: 1.0 mL/min; Column Temp: 25.0° C.,
  Mobile Phase: A=0.1% TFA (Aq), B=ACN,
  Gradient (Time/% B): 0/2, 2/2, 15/70, 20/95, 25/100, 30/100, 32/2, 42/2.
Preparative HPLC Method
  Preparative HPLC was performed on phenomenex luna 5µ 100 A° column (250 mm×21.2 mm, 5 µm), Flow rate: 15.0 mL/min. The elution conditions used are: Buffer A: 0.1% formic acid in water, Buffer B: Acetonitrile, Equilibration of the column with 0% buffer B and elution by a gradient of 0% to 10% buffer B during 30 min.

LCMS was performed on AP1 2000 LC/MS/MS triple quad with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

LCMS was performed on AP1 2000 LC/MS/MS triple quad (Applied biosystems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

An embodiment of the present invention provides the preparation of compounds of formula (I) according to the procedures of the following example(s), using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The starting materials are generally available from commercial sources such as Sigma-Aldrich, India or Germany; Combi-Blocks USA, Ark Pharm USA, Chem-Impex USA; G.L. Biochem, China and Spectrochem, India.

Example 1

(((S)-4-amino-1-(3-((S)-1,5-diaminopentyl)-1,2,4-oxadiazol-5-yl)-4-oxobutyl)carbamoyl)-L-proline
(Compound 1)

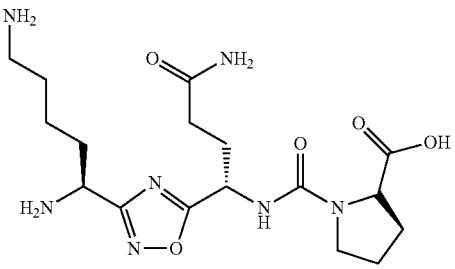

Synthesis of Compound 1 b

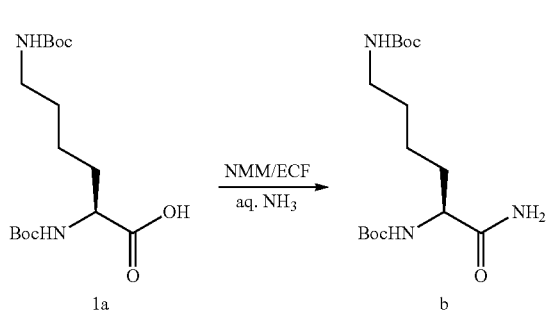 [SMILES: CC(C)(C)OC(=O)NCCCC[C@H](NC(=O)OC(C)(C)C)C(=O)O ; CC(C)(C)OC(=O)NCCCC[C@H](NC(=O)OC(C)(C)C)C(N)=O]

Ethylchloroformate (2.47 mL, 25.9 mmol) and NMM (2.9 mL, 25.9 mmol) were added to a solution of compound 1a (6.0 g, 17.3 mmol) in THF (60 mL) and stirred at −20° C. for 20 min. After 20 minutes 25% of aq.ammonia (24 mL) was added to the active mixed anhydride resulting from the reaction and the reaction mass was stirred at 0-5° C. for 30 min. The completeness of the reaction was confirmed by TLC analysis. The volatiles were evaporated under reduced pressure and partitioned between water and ethyl acetate. The organic layer was washed with NaHCO$_3$ solution followed by citric acid solution and brine solution. The separated organic layer was dried over Na$_2$SO$_4$, filtered and evaporated under reduced pressure to yield 5.6 g of compound 1 b. LCMS: 346.4 [M+H]$^+$.

Synthesis of Compound 1C

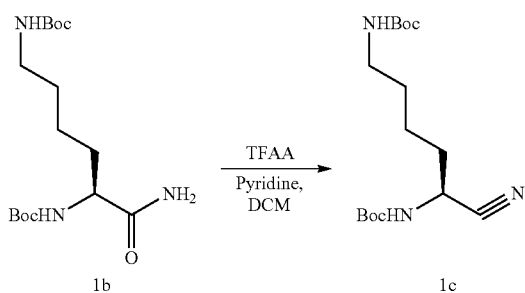 [SMILES: CC(C)(C)OC(=O)NCCCC[C@H](NC(=O)OC(C)(C)C)C(N)=O ; "TFAA" ; CC(C)(C)OC(=O)NCCCC[C@@H](C#N)NC(=O)OC(C)(C)C]

Trifluroacetic anhydride (6.85 mL, 48.6 mmol) was added to a solution of compound 1b (5.6 g, 16.2 mmol), pyridine (7.84 mL, 97.2 mmol) in DCM (60 mL) at 0° C. and stirred at room temperature for an hour. The completion of the reaction was confirmed by TLC analysis. The volatiles were evaporated under reduced pressure and partitioned between water and CH$_2$Cl$_2$. The organic layer was washed with NaHCO$_3$ solution followed by citric acid and brine solution. The separated organic layer was dried over Na$_2$SO$_4$, filtered and evaporated under reduced pressure to yield 5.42 g of compound 1c, which was used for next step directly.

Synthesis of Compound 1d

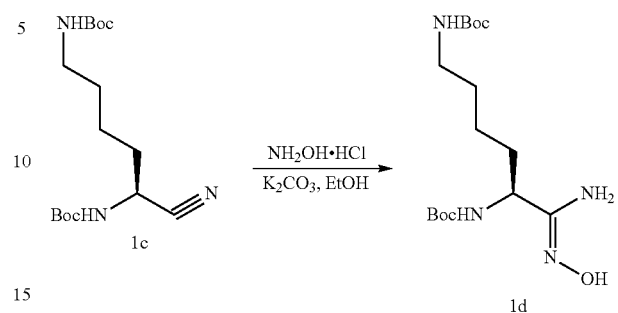

Hydroxylamine hydrochloride (3.43 g, 49.5 mmol), water (10 mL) and K$_2$CO$_3$ (4.54 g, 32.9 mmol) were added to a solution of compound 1c (5.4 g, 16.5 mmol) in EtOH (60 mL) and stirred at room temperature for overnight. The completion of the reaction was confirmed by TLC analysis. After the completion of reaction, the compound from the water was extracted by using the CH$_2$Cl$_2$ followed washing the organic layer with water, brine and concentrated under reduced pressure to yield 5.8 g of compound 1d. LCMS: 361.3 [M+H]$^+$.

Synthesis of Compound 1f

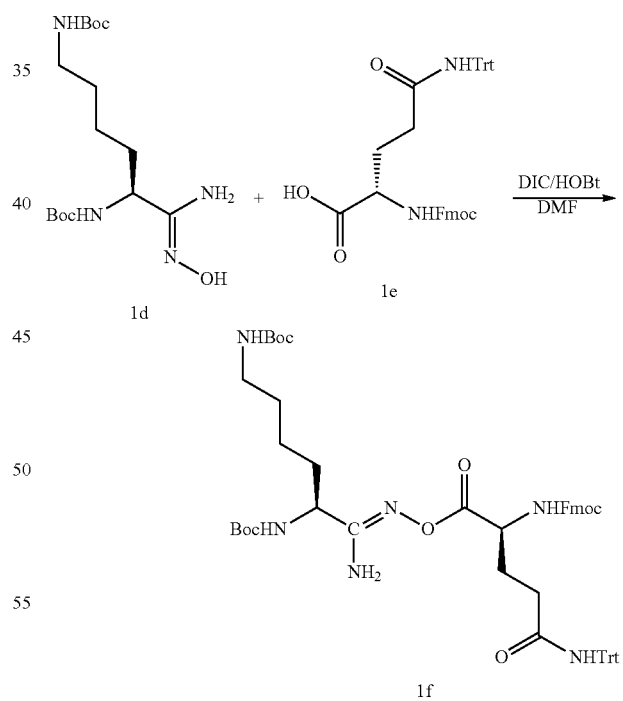

HOBt (3.24 g, 24.0 mmol) and DIC (3.36 mL, 24.0 mmol) were added to a solution of Fmoc-Gln(Trt)-OH (compound 1e) (9.83 g, 16.1 mmol) in DMF (100 mL) at 0° C. and stirred for 15 min. Compound 1d (5.8 g, 16.1 mmol) was added to the reaction mass at the same temperature and the resulting mixture was stirred for an hour at the same temperature, followed by stirring at room temperature for an additional 2 h. The completion of the reaction was confirmed by TLC analysis. The reaction mixture was quenched with ice water; precipitated white solid was filtered; washed with water (150 mL) and dried under high under reduced pressure to yield 8.62 g of compound 1f. LCMS: 953.7 [M+H]⁺.

Synthesis of Compound 1g

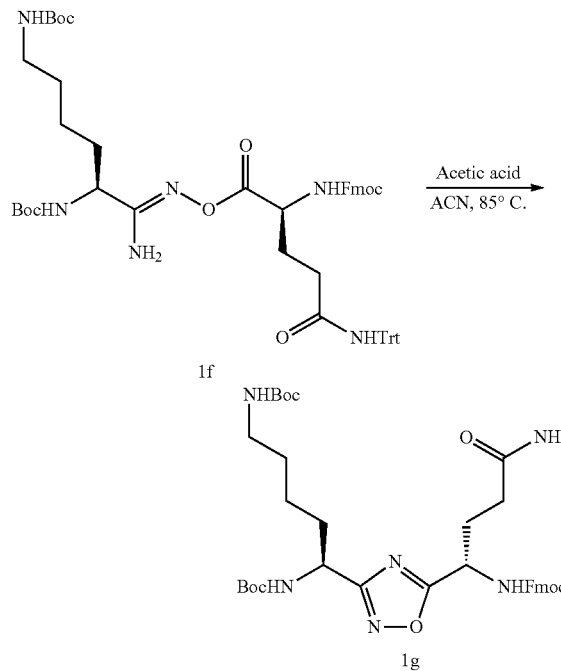

Acetic acid (5 mL) was added to a solution of compound 1f (5.0 g, 5.0 mmol) in acetonitrile (50 ml) at room temperature and the reaction mass was refluxed at 85° C. for 12 h. The completion of the reaction was confirmed by TLC analysis. The volatiles were evaporated under reduced pressure to obtain crude semi solid which was diluted with water and ethyl acetate. The organic layer was washed with NaHCO₃ solution followed by citric acid and brine solution. The organic layer was dried over Na₂SO₄; filtered and evaporated under reduced pressure to obtain crude solid. Compound was purified using column chromatography to yield 4.3 g of title compound. LCMS: 935.6 [M+H]⁺.

Synthesis of Compound 1h

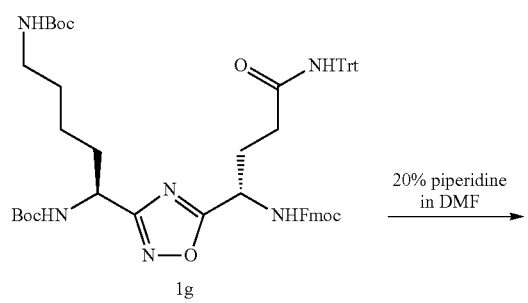

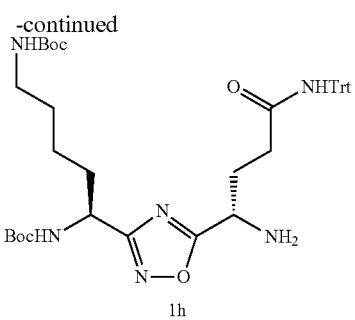

Compound 1g (4.3 g, 4.5 mmol) was added to a solution of 20% piperidine in DMF (20 mL) at 0° C. and the reaction mass was stirred at same temperature for an hour. The completion of the reaction was confirmed by TLC analysis. After completion, the reaction mixture was quenched with ice-cold water and the resulting white precipitate was filtered and dried under vacuum. The crude product obtained was diluted with hexane, stirred and filtered to yield 3.0 g of compound 1h. LCMS: 713.4 [M+H]⁺.

Synthesis of Compound 1i

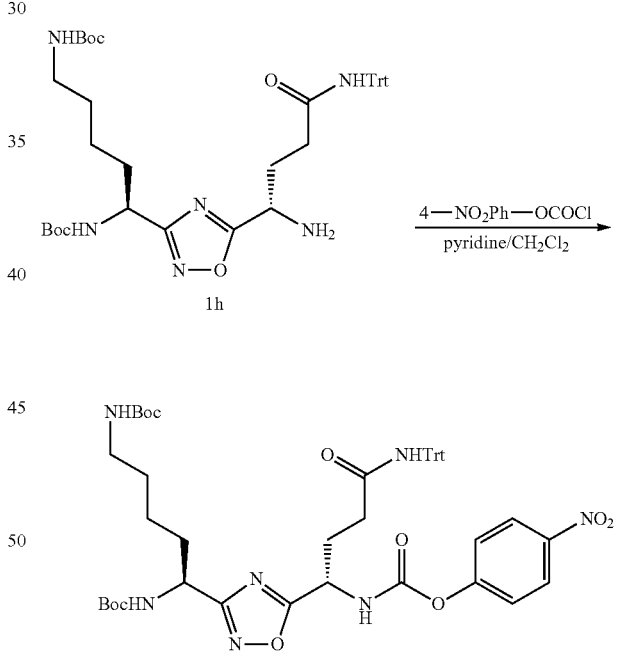

Pyridine (0.33 mL, 4.2 mmol) was added to a solution of compound 1h (1.5 g, 2.1 mmol) in CH₂Cl₂ (15 mL) and the resulting solution was stirred at room temperature for 10 min. 4-nitrophenyl chloroformate (0.84 g, 4.2 mmol) in CH₂Cl₂ (15 mL) was added to the above mixture and the resultant mixture was stirred at room temperature for an hour. After completion of reaction (confirmed by TLC), it was diluted with CH₂Cl₂ (50 mL) and washed with water (100 mL×2), 1N HCl (100 mL×2), water followed by brine

Synthesis of Compound 1j

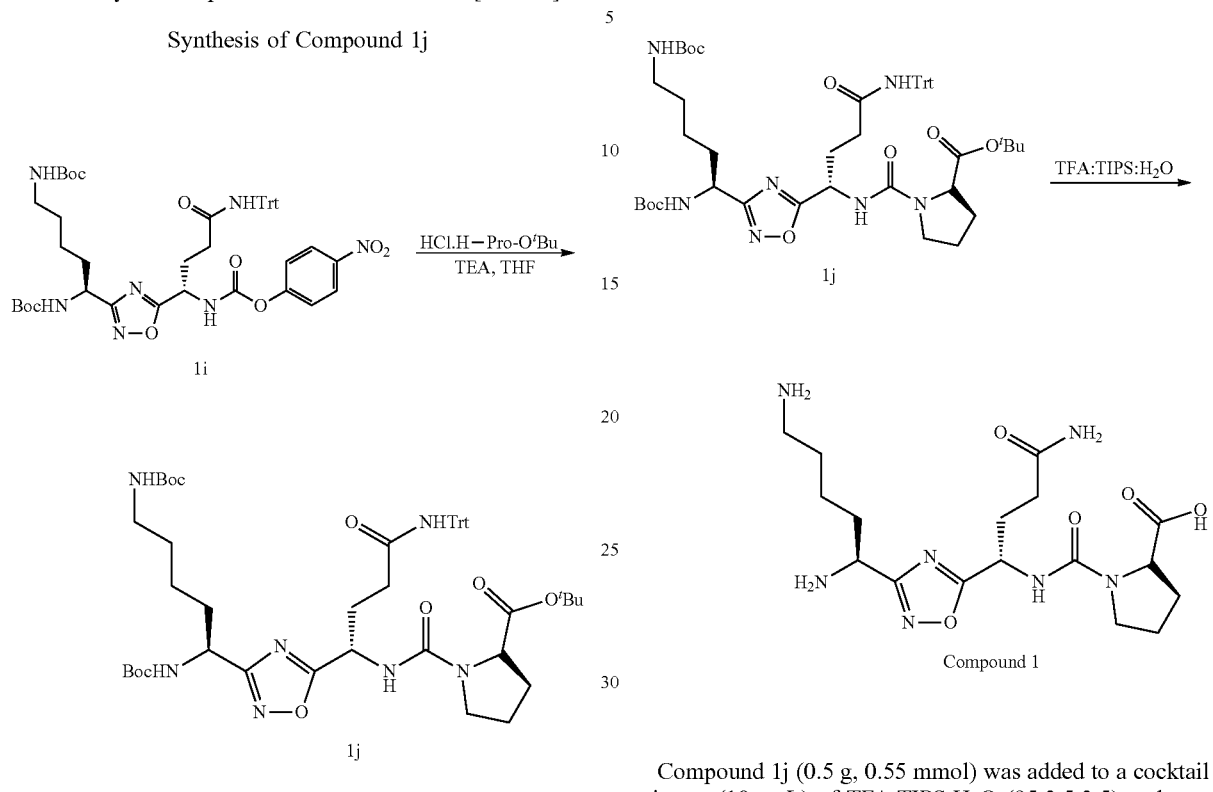

TEA (0.34 mL, 2.46 mm) was added to a solution of H-Pro-O$^t$Bu.HCl (0.21 g, 1.23 mmol) and compound 1i (0.72 g, 0.82 mmol) in THF (10 mL) at room temperature and stirred for 12 h. The volatiles were evaporated and portioned between ethyl acetate and water. The reaction mixture was diluted with ice cold water and extracted with EtOAc. The Organic layer was separated and dried over Na$_2$SO$_4$ and concentrated under reduced pressure. The crude compound obtained was purified by column chromatography and compound elutes in 50% of ethyl acetate in hexane. Yield: 0.5 g of compound 1j. LCMS: 910.6 [M+H]$^+$.

Synthesis of Compound 1

Compound 1j (0.5 g, 0.55 mmol) was added to a cocktail mixture (10 m L) of TFA:TIPS:H$_2$O (95:2.5:2.5) and was stirred at room temperature for 3 h. The resulting reaction mixture was evaporated under reduced pressure, diluted with diethyl ether and filtered to yield 0.2 g of crude compound 1. The crude solid material was purified by preparative HPLC method described under experimental conditions. LCMS: 412.2 [M+H]$^+$. HPLC t$_R$ (min): 9.6.

The below compounds were prepared by procedure similar to the one described in Example 1 (compound 1) with appropriate variations in reactants, quantities of reagents, solvents and reaction conditions. The characterization data of the compounds are summarized herein below table.

| Compound | Structure | Observed Mass [M + H]$^+$ |
|---|---|---|
| 2. | 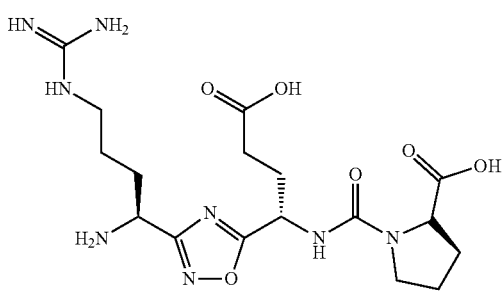 | 441.4 |

Earlier in text (page 55):

solution (100 mL×2). The organic layer was dried over Na$_2$SO$_4$; filtered and evaporated under reduced pressure to yield 0.72 g compound 1i, which was taken to the next step without any further purification. LCMS: 878.9 [M−100].

-continued

| Compound | Structure | Observed Mass [M + H]+ |
|---|---|---|
| 3. | 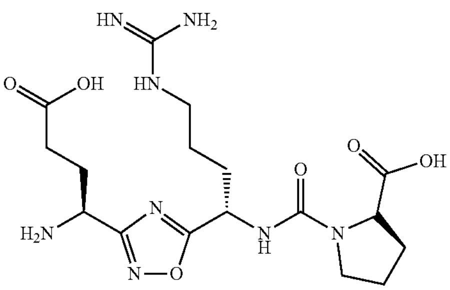 | 441.2 |
| 4. | 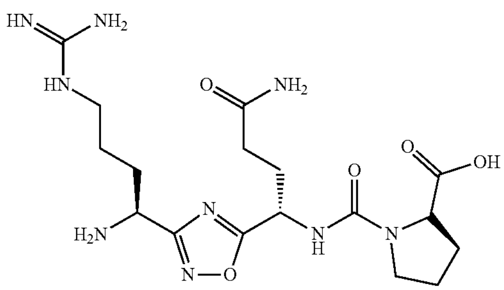 | 440.3 |
| 5. | 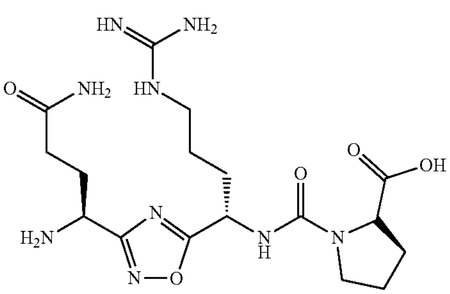 | 440.5 |
| 6. | 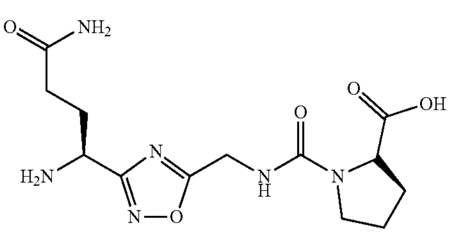 | 341.4 |

Example 2

(S)-4-(3-((S)-1-amino-4-guanidinobutyl)-1,2,4-oxadiazol-5-yl)-4-(3-((S)-1-carboxy-2-phenylethyl)ureido)butanoic Acid (Compound 7)

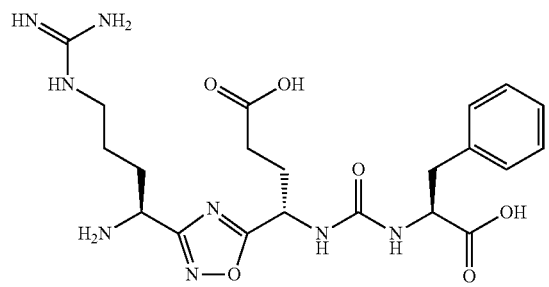 [SMILES: N=C(N)NCCC[C@H](N)c1noc([C@H](CCC(=O)O)NC(=O)N[C@@H](Cc2ccccc2)C(=O)O)n1]

Synthesis of Compound 2b

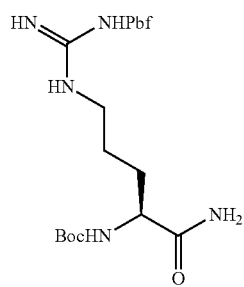

Ethylchloroformate (1.75 mL, 18.23 mmol) and NMM (2.0 mL, 18.23 mmol) were added into a solution of compound 2a (8.0 g, 15.18 mmol) in THF (45 mL) and the resulting mixture was stirred at −20° C. for 20 min. After 20 minutes 25% of aqueous ammonia (25 mL) was added to the active mixed anhydride generated and stirred at 0-5° C. for 30 min. The completeness of the reaction was confirmed by TLC analysis. The volatiles were evaporated under reduced pressure and partitioned between water and ethyl acetate. The organic layer was washed with NaHCO$_3$ solution followed by citric acid solution and brine solution. The separated organic layer was dried over Na$_2$SO$_4$, filtered and evaporated under reduced pressure to yield 7.1 g of compound 2b. LCMS: 526.3 [M+H]$^+$.

Synthesis of Compound 2c

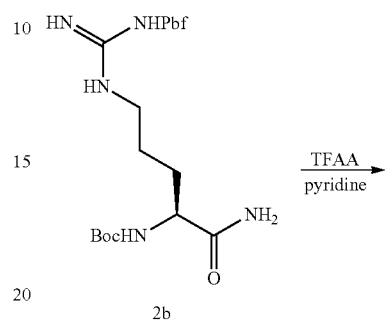

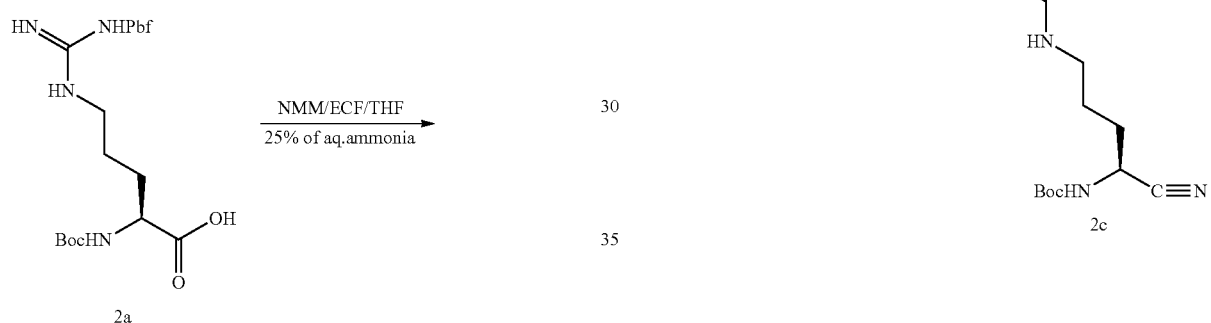

Trifluroacetic anhydride (TFAA) (2.83 mL, 20.26 mmol) was added to a solution of compound 2b (7.1 g, 13.51 mmol) in pyridine (7.08 g, 87.80 mmol) and the resulting mixture was stirred at room temperature for 2 h. The completion of the reaction was confirmed by TLC analysis. The volatiles were evaporated under reduced pressure and partitioned between water and ethyl acetate. The organic layer was washed with citric acid and brine solution. The separated organic layer was dried over Na$_2$SO$_4$, filtered and evaporated under reduced pressure. The crude solid was purified via column chromatography (60-120 silicagel) to yield 5.8 g of compound 2c. LCMS: 508.3 [M+H]$^+$.

Synthesis of Compound 2d

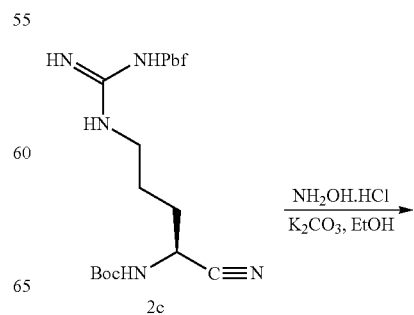

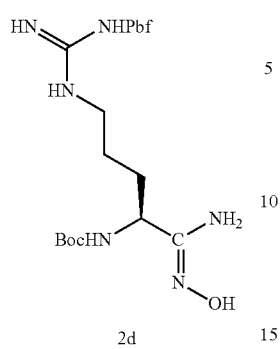

2d

Hydroxylamine hydrochloride (1.56 g, 22.50 mmol), water (30 mL) and potassium carbonate (3.11 g, 11.25 mmol) were added to a solution of compound 2c (5.8 g, 11.25 mmol) in EtOH (60 mL) and stirred at 90° C. for 3 h. The completion of the reaction was confirmed by TLC analysis. The volatiles were evaporated under reduced pressure and partitioned between water and ethyl acetate. The organic layer was washed with brine solution, dried over Na$_2$SO$_4$ then filtered and evaporated under reduced pressure, the solid obtained was washed with 20% ethyl acetate to yield 6.1 g of compound 2d. LCMS: 541.3 [M+H]$^+$.

Synthesis of Compound 2f

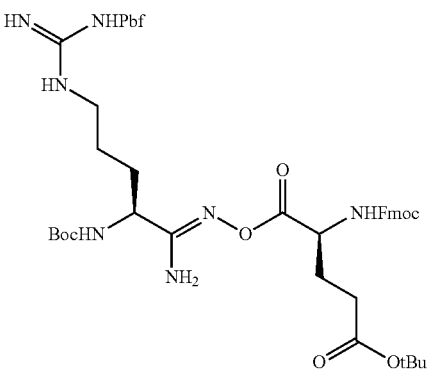

2f

HOBt (2.28 g, 16.9 mmol) and DIC (2.62 mL, 16.9 mmol) were added to a solution of Fmoc-Glu(O$^t$Bu)-OH (compound 2e) (4.0 g, 9.02 mmol) in DMF (60 mL) at 0° C. and the resulting mixture was stirred for 15 min. Then compound 2d (6.1 g, 11.28 mmol) was added to the above mixture at the same temperature and the reaction mixture was continued stirring for an hour and then at room temperature for 2 h. The completion of the reaction was confirmed by TLC analysis. The reaction mixture was quenched with ice cold water, the precipitated white solid was filtered, washed with water (150 mL) and dried under high under reduced pressure. The solid was taken into 10% MeOH in DCM and washed the organic layer with 10% NaHCO$_3$, water and brine solution. The organic layer was dried over Na$_2$SO$_4$ and concentrated under reduced pressure to yield 8.0 g of compound 2f. LCMS: 948.7 [M+H]$^+$.

Synthesis of Compound 2g

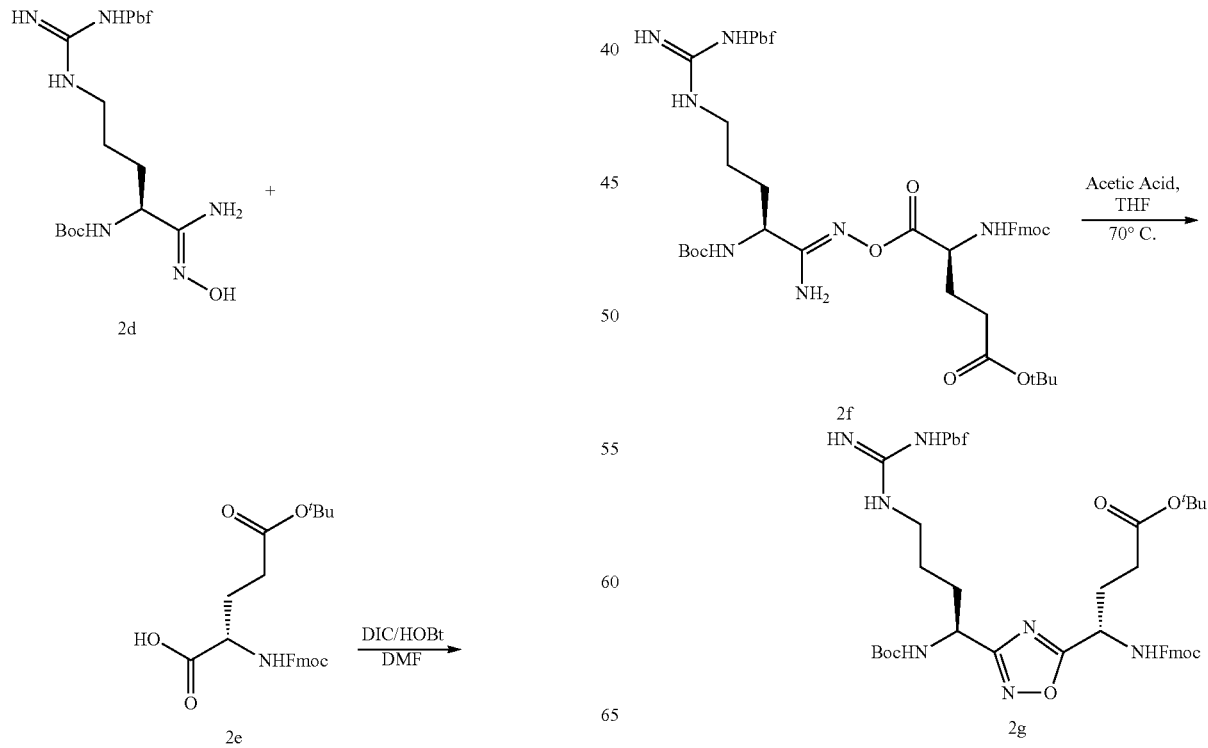

Acetic acid (7 mL) was added to a solution of compound 2f (7.0 g, 7.38 mmol) in THF (70 ml) at room temperature and the resulting mixture was refluxed at 70° C. for 12 h. The completion of the reaction was confirmed by TLC analysis. The volatiles were evaporated under reduced pressure to obtain crude semi solid which was diluted with water and ethyl acetate. The organic layer was washed with NaHCO$_3$ solution followed by brine solution. The organic layer was dried over Na$_2$SO$_4$, filtered and evaporated under reduced pressure to get crude solid. The compound was purified by column chromatography (60-120 silicagel) to yield 5.4 g of compound 2g. LCMS: 930.5 [M+H]$^+$.

Synthesis of Compound 2h

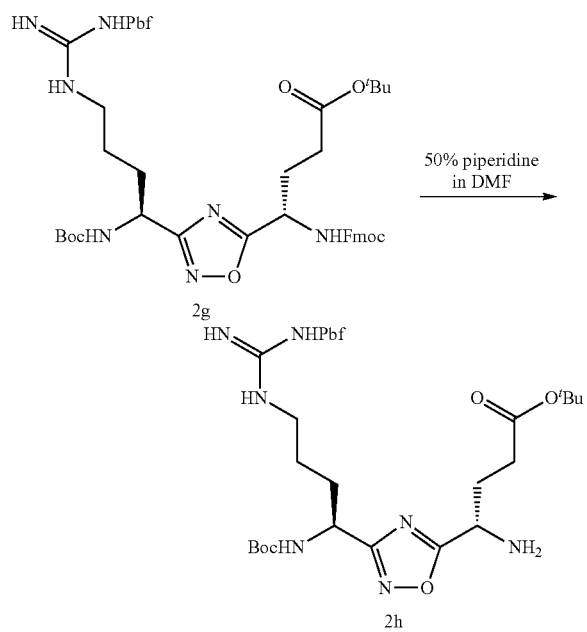

Compound 2g (5.4 g, 5.80 mmol) was added to a solution of 50% piperidine in DMF (20 mL) at 0° C. and stirred at same temperature for 2 h. The completion of the reaction was confirmed by TLC analysis. The reaction mass was quenched with water (100 mL), the resulted precipitate was filtered. The solid obtained was dissolved in ethyl acetate and washed the organic layer with 10% NaHCO$_3$, water and brine. The organic layer was dried over Na$_2$SO$_4$ and concentrated under reduced pressure. The crude product obtained was diluted with hexane and the resulted precipitate was filtered followed by washing with hexane to obtain 3.0 g of compound 2h. LCMS 708.6 [M+H]$^+$.

Synthesis of Compound 2i

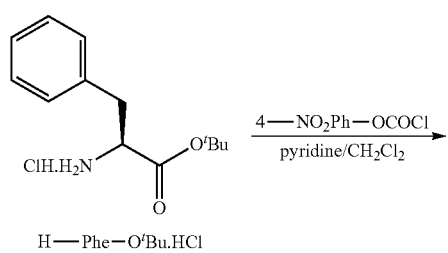

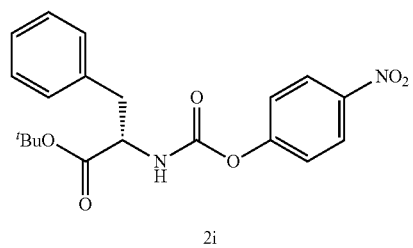

Pyridine (0.75 mL, 9.3 mmol) was added to a solution of H-Phe-O$^t$Bu.HCl (2.0 g, 7.75 mmol) in CH$_2$Cl$_2$ (20 mL) was added pyridine and the resulting solution was stirred at room temperature for 10 min. To this reaction mixture a solution of 4-nitrophenyl chloroformate (1.87 g, 9.30 mmol) in CH$_2$Cl$_2$ (20 mL) was added and the resultant mixture was stirred at room temperature for 3 h. After completion of reaction (confirmed by TLC) it was diluted with CH$_2$Cl$_2$ (50 mL) and washed with water (100 mL×2), 10% citric acid (100 mL×2), water (100 mL), followed by brine solution (100 mL). The organic layer was dried over Na$_2$SO$_4$, filtered and evaporated under reduced pressure to yield 1.7 g compound 2i, which was taken to the next step without any further purification.

Synthesis of Compound 2j

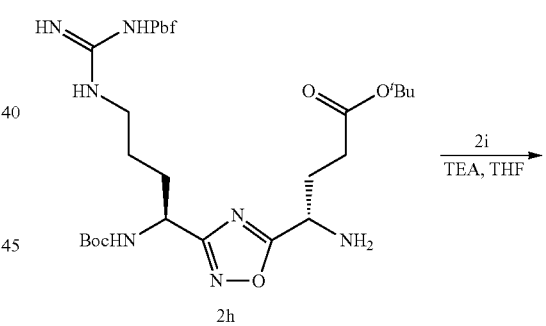

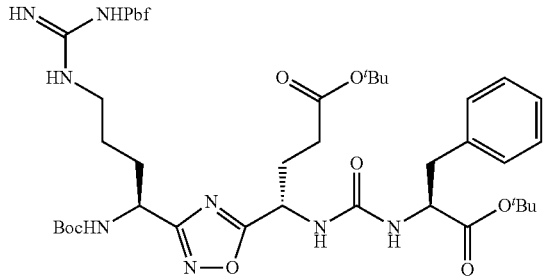

TEA (0.29 mL, 2.1 mmol) was added to a solution of compound 2h (1.0 g, 1.41 mmol) and compound 2i (0.54 g, 1.41 mmol) in THF (10 mL) at room temperature and stirred for 3 h. The volatiles were evaporated and portioned between EtOAc and water. The reaction mixture was diluted with ice cold water and extracted with EtOAc followed by washing with 10% K₂CO₃ (100 mL×4), water and brine solution. Organic layer separated and dried over Na₂SO₄ and concentrated under reduced pressure. The crude product obtained was diluted with hexane and the resulted precipitate was filtered followed by washing with hexane yielded 0.98 g of compound 2j. LCMS: 955.6 [M+H]⁺.

Synthesis of Compound 7

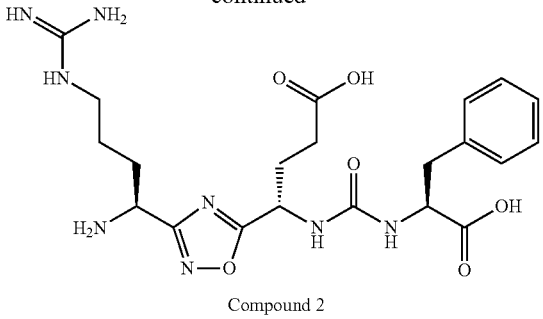

Compound 2

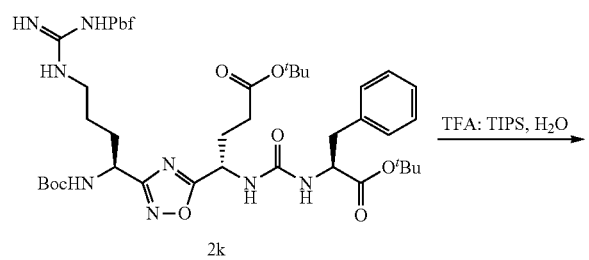

Compound 2j (0.5 g, 5.2 mmol) was added to cocktail mixture (5 m L) of trifluoroacetic: TIPS:water (95:2.5:2.5). The cleavage solution was stirred at room temperature for 3 h. The resulting reaction mixture was evaporated under reduced pressure, diluted with diethyl ether and filtered to yield 0.34 g of crude compound 2. The crude solid material was purified by preparative HPLC method as described under experimental conditions. LCMS: 491.1 [M+H]⁺. HPLC $t_R$: (min): 11.1

The below compounds were prepared by procedure similar to the one described in Example 2 (Compound 7) with appropriate variations in reactants, quantities of reagents, solvents and reaction conditions. The characterization data of the compounds are summarized herein below table.

| Compound | Structure | Observed Mass [M + H]⁺ |
|---|---|---|
| 8. | 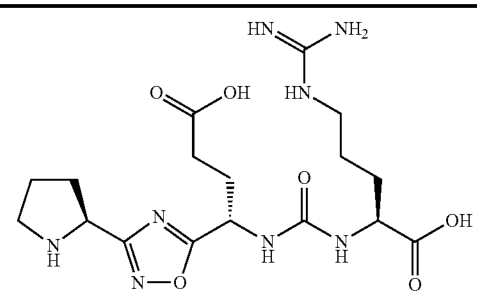 | 441.25 |
| 9. | 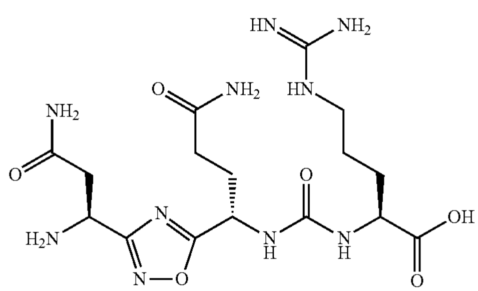 [SMILES: N=C(N)NCCC[C@H](NC(=O)N[C@@H](CCC(N)=O)c1nc([C@@H](N)CC(N)=O)no1)C(=O)O] | 457.2 |
| 10. | 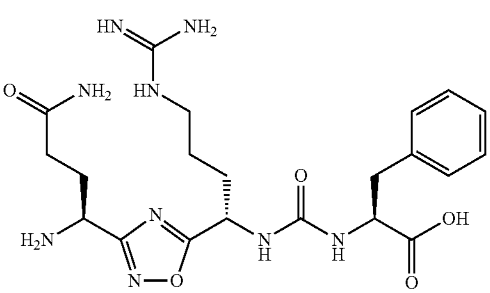 [SMILES: N=C(N)NCCC[C@H](NC(=O)N[C@@H](Cc1ccccc1)C(=O)O)c1nc([C@@H](N)CCC(N)=O)no1] | 490.6 |

-continued

| Compound | Structure | Observed Mass [M + H]⁺ |
|---|---|---|
| 11. | 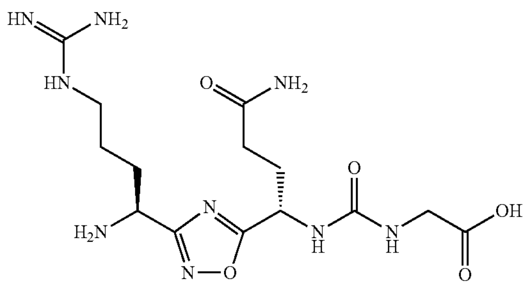 [SMILES: N=C(N)NCCC[C@H](N)c1noc([C@H](CCC(N)=O)NC(=O)NCC(=O)O)n1] | 400.3 |
| 12. | 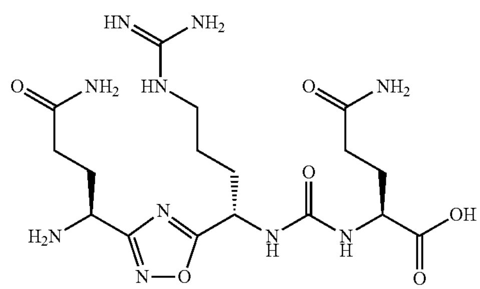 [SMILES: N=C(N)NCCC[C@H](NC(=O)N[C@@H](CCC(N)=O)C(=O)O)c1nc([C@@H](N)CCC(N)=O)no1] | 471.7 |
| 13. | 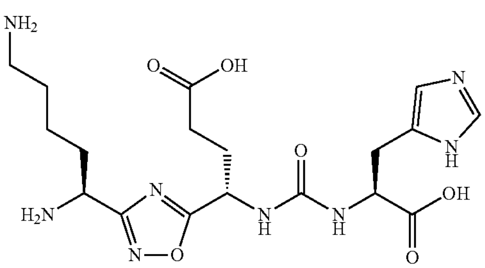 [SMILES: NCCCC[C@H](N)c1noc([C@H](CCC(=O)O)NC(=O)N[C@@H](Cc2cnc[nH]2)C(=O)O)n1] | 453.8 |
| 14. | 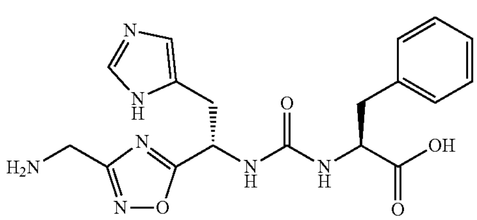 [SMILES: NCc1noc([C@H](Cc2cnc[nH]2)NC(=O)N[C@@H](Cc2ccccc2)C(=O)O)n1] | 400.2 |
| 15. | 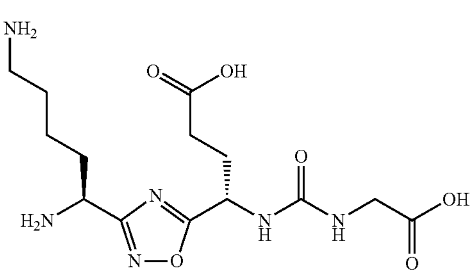 [SMILES: NCCCC[C@H](N)c1noc([C@H](CCC(=O)O)NC(=O)NCC(=O)O)n1] | 373.0 |

The below compounds were also prepared by procedure similar to the one described in Example 1 (compound 1) with appropriate variations in reactants, quantities of reagents, solvents and reaction conditions. The characterization data of the compounds are summarized herein below table.

| Compound | Structure | Observed Mass |
|---|---|---|
| 16 | 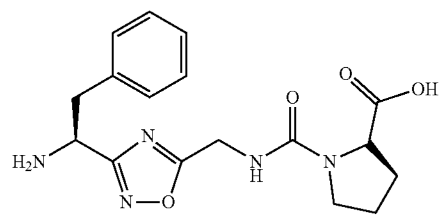 | 360.1 (M + 1) |
| 17 | 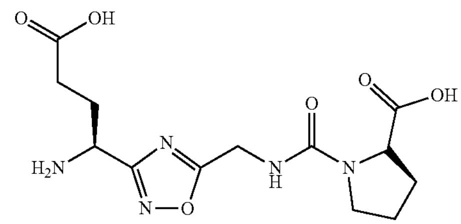 | 342.3 (M + 1) |
| 19 | 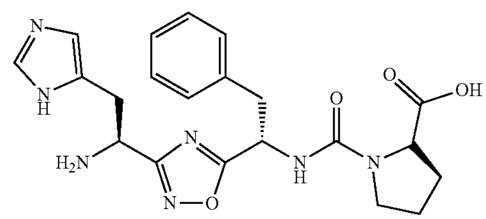 | 439.9 (M + 1) |
| 20 | 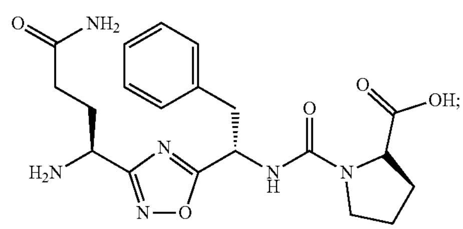 | 431.0 (M + 1) |
| 21 | 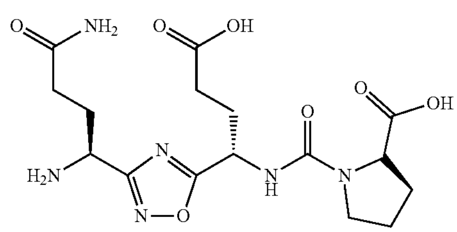 | 413.1 (M + 1) |
| 22 | 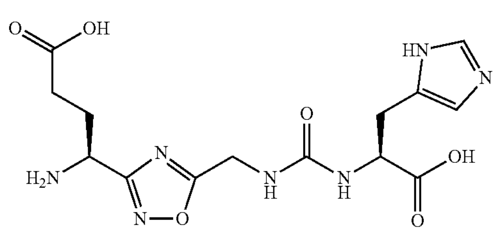 [SMILES: N[C@@H](CCC(=O)O)c1noc(CNC(=O)N[C@@H](Cc2cnc[nH]2)C(=O)O)n1] | 382.0 (M + 1) |

-continued

| Compound | Structure | Observed Mass |
|---|---|---|
| 23 | 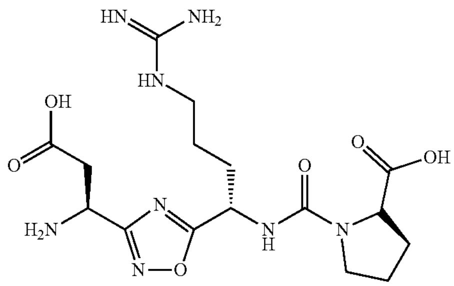 | 427.0 (M + 1) |
| 24 | 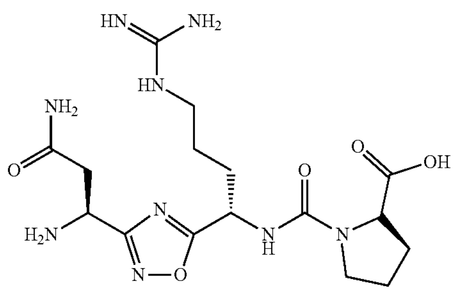 | 473.4 (M + 1) |
| 25 | 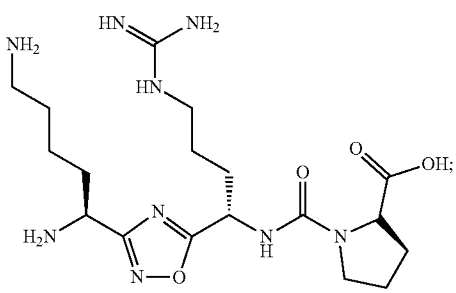 | 440.5 (M + 1) |
| 27 | 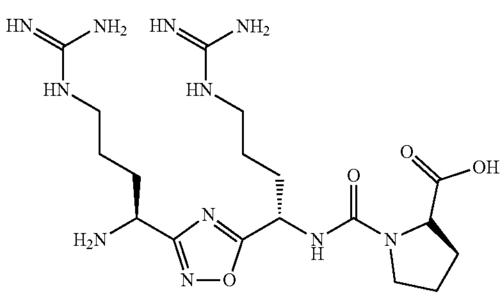 | 468.5 (M + 1) |
| 28 | 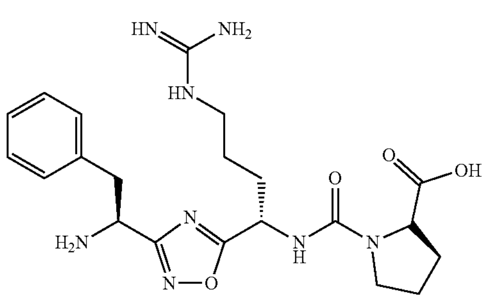 | 459.5 (M + 1) |

-continued

| Compound | Structure | Observed Mass |
|---|---|---|
| 29 | 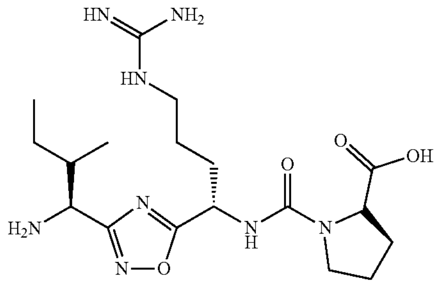 | 425.4 (M + 1) |
| 30 | 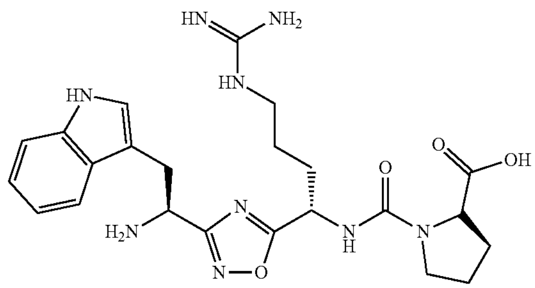 | 498.4 (M + 1) |
| 31 | 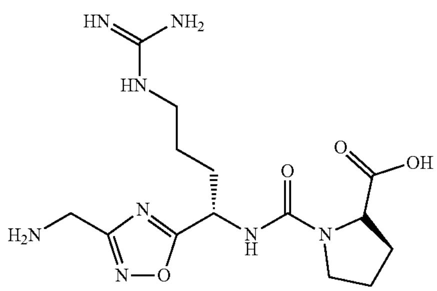 | 369.4 (M + 1) |
| 32 | 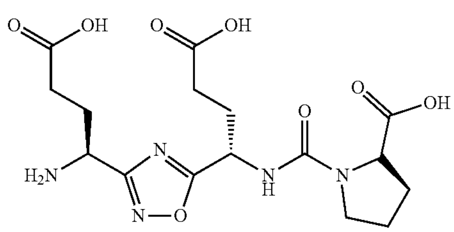 | 414.3 (M + 1) |
| 33 | 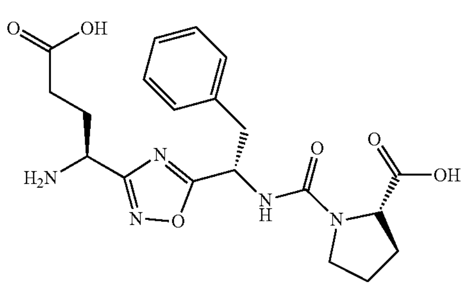 | 432.3 (M + 1) |

-continued

| Compound | Structure | Observed Mass |
|---|---|---|
| 35 | 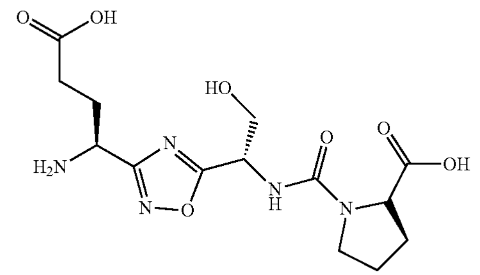 | 372.0 (M + 1) |
| 36 | 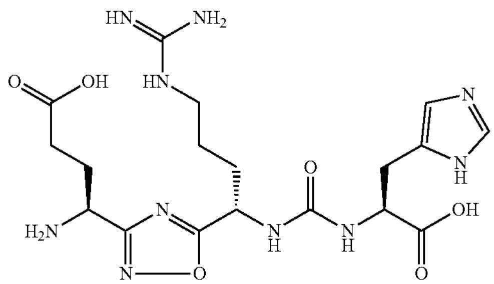 [SMILES: N=C(N)NCCC[C@H](NC(=O)N[C@@H](Cc1cnc[nH]1)C(=O)O)c1nc([C@@H](N)CCC(=O)O)no1] | 480.8 (M + 1) |
| 37 | 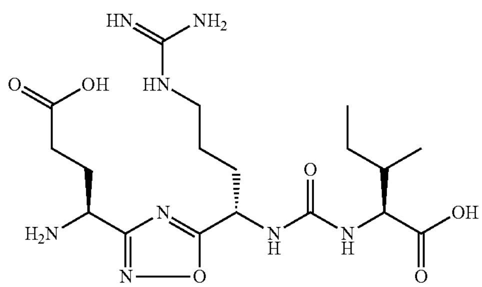 [SMILES: CCC(C)[C@H](NC(=O)N[C@@H](CCCNC(=N)N)c1nc([C@@H](N)CCC(=O)O)no1)C(=O)O] | 457.4 (M + 1) |
| 38 | 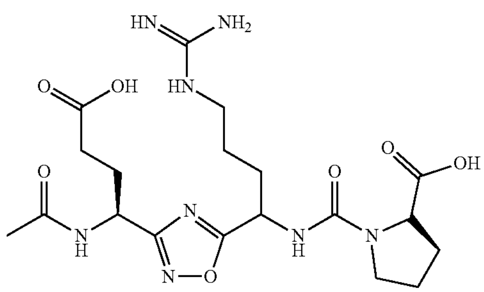 | 483.4 (M + 1) |
| 39 | 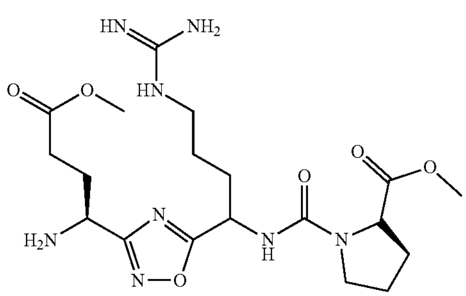 | 469.3 (M + 1) |

| Compound | Structure | Observed Mass |
|---|---|---|
| 40 | (structure) | 455.3 (M + 1) |

The below compounds were also prepared by procedure similar to the one described in Example 2 (Compound 7) with appropriate variations in reactants, quantities of reagents, solvents and reaction conditions. The characterization data of the compounds are summarized herein below table.

| Compound | Structure | Observed Mass |
|---|---|---|
| 41 | (structure) | 372.3 (M + 1) |
| 42 | (structure) | 372.3 (M + 1) |
| 43 | (structure) | 429.3 (M + 1) |
| 44 | (structure) | 457.3 (M + 1) |

-continued

| Compound | Structure | Observed Mass |
|---|---|---|
| 45 | 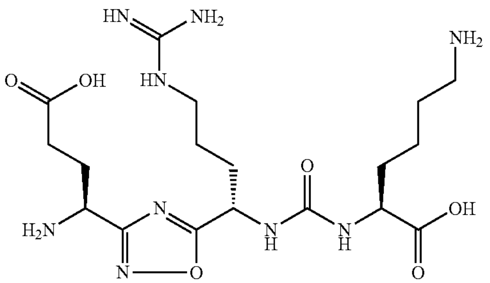 [SMILES: N=C(N)NCCC[C@H](NC(=O)N[C@@H](CCCCN)C(=O)O)c1nc([C@@H](N)CCC(=O)O)no1] | 472.3 (M + 1) |
| 46 | 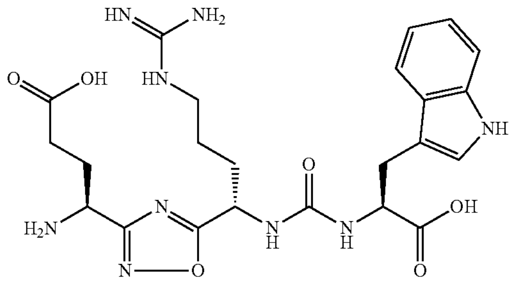 [SMILES: N=C(N)NCCC[C@H](NC(=O)N[C@@H](Cc1c[nH]c2ccccc12)C(=O)O)c1nc([C@@H](N)CCC(=O)O)no1] | 530.3 (M + 1) |
| 47 | 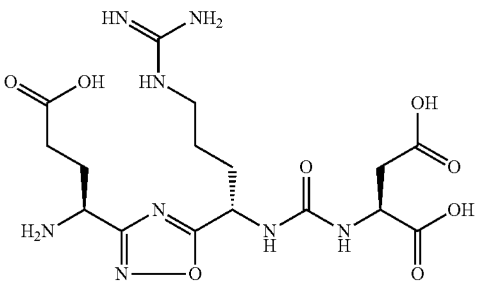 [SMILES: N=C(N)NCCC[C@H](NC(=O)N[C@@H](CC(=O)O)C(=O)O)c1nc([C@@H](N)CCC(=O)O)no1] | 459.1 (M + 1) |
| 48 | 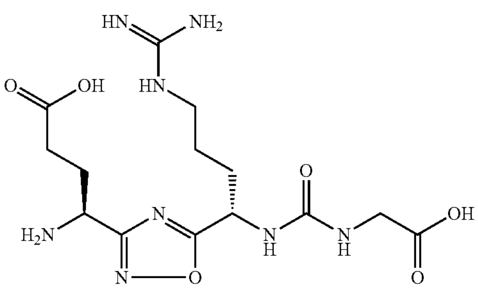 [SMILES: N=C(N)NCCC[C@H](NC(=O)NCC(=O)O)c1nc([C@@H](N)CCC(=O)O)no1] | 401.0 (M + 1) |
| 49 | 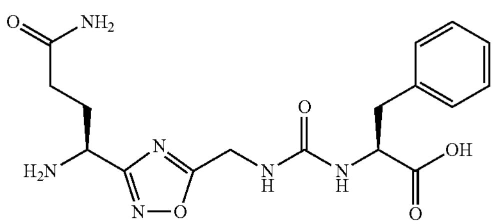 [SMILES: NC(=O)CC[C@H](N)c1noc(CNC(=O)N[C@@H](Cc2ccccc2)C(=O)O)n1] | 491.3 (M + 1) |
| 50 | 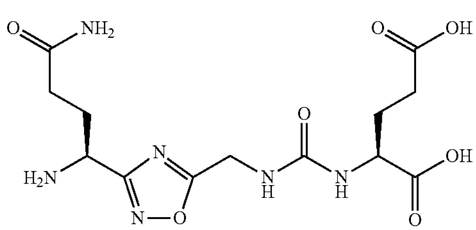 [SMILES: NC(=O)CC[C@H](N)c1noc(CNC(=O)N[C@@H](CCC(=O)O)C(=O)O)n1] | 373.2 (M + 1) |

-continued

| Compound | Structure | Observed Mass |
|---|---|---|
| 51 | 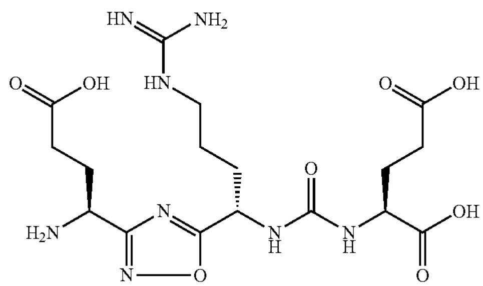 [SMILES: N=C(N)NCCC[C@H](NC(=O)N[C@@H](CCC(=O)O)C(=O)O)c1nc([C@@H](N)CCC(=O)O)no1] | 473.4 (M + 1) |
| 52 | 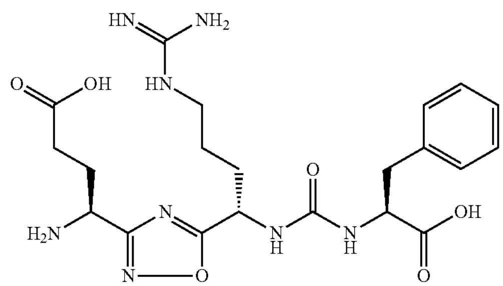 [SMILES: N=C(N)NCCC[C@H](NC(=O)N[C@@H](Cc1ccccc1)C(=O)O)c1nc([C@@H](N)CCC(=O)O)no1] | 473.4 (M + 1) |

Example 3

Percentage Rescue of Phagocytosis
Reagents

DPBS (Gibco), RPMI 1640 WITH HEPES AND L-GLN-500 ML (Lonza), Recombinant Human M-CSF (R& D systems), CD47 Monoclonal Antibody (B6H12), Functional Grade antibody (Ebioscience), Mouse IgG1 kappa Isotype Control, Functional Grade (Ebioscience), Vacutainer (multiple sample luer adapter) (BD), Vacutainer (sodium heparin (NH) 158USP units, Blood collection tubes (BD,), Histopaque (density-1.077 gm/ml) (SIGMA 1077), Trypan Blue solution (SIGMA-T8154), Hemacytometer (Bright line-SIGMA Z359629), Scalp vein infusion set (JMS), Cell Dissociation buffer (Gibco), 48-well sterile flat bottom plates (Corning), Luciferase expressing Raji cells (Generated in house by trasfection of luciferase gene in Raji cells) Luminometer, Hygromycin B (Invitrogen), Bright Glo luciferase assay system (Promega), 96 well plate, polystyrene, high band, white flat bottom wells (Sigma CLS3912), APC anti-mouse/human CD11 b Antibody (Biolegend), H929 cells, CFSE (Ebioscience), Fetal Bovine Serum (Gibco Cat #: 10437028), Round-Bottom FACs Tubes (BD), Flowcytometer BD FACS Verse, 96 well plates, ultra-low attachment (Corning).

Protocol—1: Luciferase Based Phagocytosis Assay

In vitro phagocytosis assay was performed to evaluate the ability of test item to enhance the phagocytic activity of macrophages. Monocytes were isolated from blood of healthy donor and cultured for 6-8 days using 10% RPMI (Roswell Park Memorial Institute) media and recombinant human M-CSF to differentiate into macrophages. Media was changed every alternate day. After differentiation, adherent macrophages were collected by gentle scraping and cultured in 10% RPMI overnight at a density of 0.1 million per well in 48 well tissue culture plate. Simultaneously, luciferase expressing Raji cells were cultured in 10% RPMI media with 100 µg/mL of hygromycin B in tissue culture flask. On the day of phagocytosis, macrophages were serum starved for 2 hours. 0.4 million luciferase expressing Raji cells per well were incubated with anti human CD47 purified B6H12 or Mouse IgG1 K Isotype Control antibody or various concentrations of test item in serum free media for 30 min at 37° C. and added into respective well of the 48 well plate seeded with macrophages. After 2 hours, cells were washed twice with PBS and 100 µL of serum free RPMI was added to each well. Additionally, 50 µL Bright Glow reagent was added to each well followed by mixing of cells and incubated for 5 min in dark. Luminescence reading was taken using plate reader after transferring the content of each well to white plate. Intensity of luminescence indicated the extent of phagocytosis. Each experimental condition was carried out in duplicate. The results for the selected compound of the invention are given in the below table.

| Compound | % normalized phagocytosis (at 10 µM) |
|---|---|
| 1 | 39 |
| 3 | 42 |
| 6 | 66 |
| 7 | 58 |
| 8 | 20 |
| 9 | 38 |
| 12 | 44 |
| 13 | 49 |
| 14 | 47 |

Protocol—2: FACS Based Phagocytosis Assay

Monocytes were isolated from blood of healthy donor and cultured for 6-8 days using 10% RPMI (Roswell Park Memorial Institute) media and recombinant human M-CSF to differentiate into macrophages. Media was changed every alternate day. Simultaneously, H929 cells were cultured in 10% RPMI media with 50 µg/mL of betamercaptoethanol in tissue culture flask. On the day of phagocytosis adherent macrophages were serum starved for 2 hours in RPMI media. Simultaneously H929 cells were stained with 0.3 µM CFSE stain. After washing, 0.2 million CFSE stained H929 cells were incubated with anti-human CD47 or Mouse IgG1 K Isotype Control antibody or various conc of test item in serum free media for 30 min at 37° C. After 2 hours of serum starvation macrophages were dissociated with cell dissociation buffer and collected by gentle scraping and added at conc of 0.05 million per well into respective wells of the ultra-low attachment 96 well plate seeded with H929 cells. Phagocytosis was allowed for 2 hours. After 2 hours, cells were washed with PBS and stained with 1 µL of anti-human CD11b-APC antibody prepared in 100 µL of PBS for 30 min in 4° C. in dark. Cells were further washed and fixed in 100 µL of fixation buffer until acquired by Flow cytometry. The extent of phagocytosis of H929 cells by human macrophages was measured by acquiring the samples by Flow cytometry. Samples acquired by Flow cytometry were analysed by using FlowJo software. Each experimental condition was carried out in duplicate. Cells positive for FITC (CFSE) and CD11b-APC were considered as phagocytosed macrophages. Raw data of % phagocytosis by macrophages were obtained in the form of excel sheet from FlowJo. % phagocytosis from isotype control (background phagocytosis) was subtracted from % phagocytosis of macrophages treated with compound as well as other controls to get corrected phagocytosis values. Corrected phagocytosis values of compound treated samples were normalized with phagocytosis of positive control (B6H12) using the formula:

% normalized phagocytosis=[(corrected % phagocytosis of compound)/(corrected phagocytosis of B6H12)*100]

| Compound | % normalized phagocytosis (at 10 µM) |
|---|---|
| 1 | 45 |
| 2 | 37 |
| 3 | 73 |
| 5 | 56 |
| 6 | 74 |
| 7 | 38 |
| 8 | 40 |
| 10 | 28 |
| 12 | 20 |
| 13 | 29 |
| 14 | 26 |
| 15 | 62 |
| 16 | 27 |
| 17 | 33 |
| 19 | 52 |
| 21 | 13 |
| 22 | 33 |
| 23 | 60 |
| 24 | 37 |
| 29 | 26 |
| 30 | 23 |
| 31 | 58 |
| 32 | 46 |
| 33 | 31 |
| 35 | 35 |
| 37 | 17 |
| 39 | 23 |
| 40 | 27 |
| 41 | 31 |
| 43 | 43 |
| 44 | 20 |
| 46 | 30 |
| 47 | 18 |
| 48 | 29 |
| 49 | 35 |

-continued

| Compound | % normalized phagocytosis (at 10 µM) |
|---|---|
| 50 | 26 |
| 51 | 24 |
| 52 | 77 |

Example 4

Efficacy of Compound 6 in A20 Syngeneic Lymphoma Model

Female Balb/c (BALB/cAnNTac) mice (6-8 weeks-old) bred in-house were used in this efficacy study in the A20 syngeneic lymphoma model. Animals were marked individually with tail marks and kept in cages that were identified by a cage card showing the study code, date of experimentation, sex and number of animals. During the experiment, the animals were weighed daily. A20 cell line (B-cell lymphoma line derived from a spontaneous reticulum cell neoplasm found in an old BALB/cAnN mouse) was procured from ATCC. When the mean tumor volumes reached approximately 75 mm$^3$, the animals were randomized based on tumour volumes into four groups of twelve animals in each group. Following randomization into various treatment groups, dosing with vehicle and Compound 6 was initiated. All treatments were administered per orally at a twice daily dosing frequency using a dose of 3 mg/kg, 10 mg/Kg and 30 mg/Kg. The treatment was continued for a period of 21 days after which the overall efficacy and tolerability were evaluated based on tumor volume and body weight changes observed during the treatment period. On treatment day 21, animals from all the treatment groups were sacrificed in sequential order at 1 hour after last dose administration.

Individual animal body weights were recorded daily before the administration of test item throughout the experimental period. Animals were observed for mortality/morbidity once daily throughout the experimental period and were also observed for clinical signs once daily throughout the experimental period. The tumor volumes were measured in all treatment group animals thrice a week (once every 2-3 days) using a digital Vernier callipers. From an ethical viewpoint, any treatment/control group with a mean tumor weight in excess of 10% of animal body weight were humanely sacrificed. As a measure of efficacy, the % T (treatment)/C(control) and % TGI (% Tumor growth inhibition) values were calculated. Graphs and statistical analysis were performed using GraphPad Prism®, Version 7.0. For analysis of tumor volume data, statistical comparison was done on Day 21 for all groups using One-way ANOVA with Dunnett's multiple comparison test. All analyses and comparisons was evaluated at the 5% (p<0.05) level. A "p" value less than 0.05 was considered as significant.

Compound 6 was well tolerated without any signs of body weight loss and/or clinical signs of toxicity. In terms of antitumor efficacy, compound 6 demonstrated statistically significant tumor growth inhibition (TGI) at all the tested dose levels. Compound 6 treatment resulted in tumor growth inhibition values of 53%, 64% and 67% at doses of 3 mg/kg, 10 mg/kg and 30 mg/kg, respectively.

Inhibition of Tumor Growth by Compound 6 in A20 Model

| Group | Compound | Dose | TGI (%) |
|---|---|---|---|
| 1 | Vehicle control | 0 mg/kg (bid) | — |
| 2 | Compound 6 | 3 mg/kg (bid) | 53* |
| 3 | Compound 6 | 10 mg/kg (bid) | 64** |
| 4 | Compound 6 | 30 mg/kg (bid) | 67** |

Statistics: one-way ANOVA, Dunnett's multiple comparison's test: *$p < 0.05$; **$p < 0.01$

What is claimed is:

1. A compound of formula (IA):

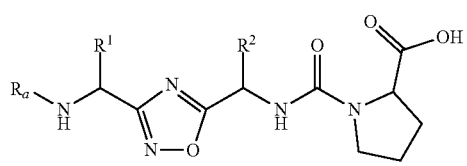

(IA)

or a pharmaceutically acceptable salt or an amide or an ester, or a stereoisomer thereof; wherein, $R_a$ is hydrogen or acyl;

$R_1$ represents hydrogen, —(CH$_2$)$_2$CONH$_2$, —(CH$_2$)$_2$COOH, —CH$_2$COOH, —(CH$_2$)$_3$NHC(=NH)NH$_2$, —(CH$_2$)$_4$NH$_2$, —CH$_2$CONH$_2$, —CH(CH$_3$)—CH$_2$—CH$_3$, —CH$_2$-aryl, or —CH$_2$— heteroaryl; wherein the said aryl and heteroaryl are unsubstituted; or $R_a$ and $R_1$, together with the atoms to which they are attached form pyrrolidine ring optionally substituted with oxo group; and $R_2$ represents —(CH$_2$)$_3$NHC(=NH)NH$_2$.

2. The compound of claim 1, wherein $R_1$ represents hydrogen, —CH$_2$—COOH, —CH$_2$—CONH$_2$, —CH(CH$_3$)—CH$_2$—CH$_3$, —(CH$_2$)$_2$CONH$_2$, —(CH$_2$)$_2$COOH, —(CH$_2$)$_3$NHC(=NH)NH$_2$, —(CH$_2$)$_4$NH$_2$, —CH$_2$-phenyl, —CH$_2$-indolyl or —CH$_2$-imidazolyl.

3. The compound of claim 1, wherein, $R_a$ is hydrogen; and $R_1$ represents hydrogen, —CH$_2$—COOH, —CH$_2$—CONH$_2$, —CH(CH$_3$)—CH$_2$—CH$_3$, —(CH$_2$)$_2$CONH$_2$, —(CH$_2$)$_2$COOH, —(CH$_2$)$_3$NHC(=NH)NH$_2$, —(CH$_2$)$_4$NH$_2$, —CH$_2$-phenyl, —CH$_2$-indolyl or —CH$_2$-imidazolyl.

4. A compound that is:

| Compound | Structure |
|---|---|
| 7 | 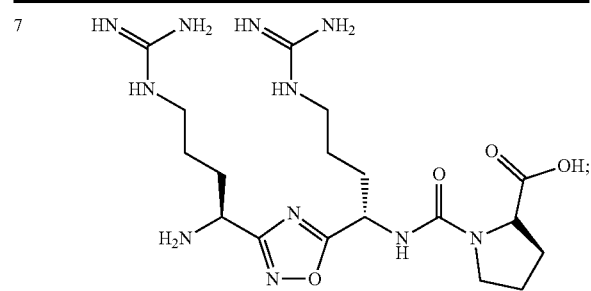 |
| 8 | 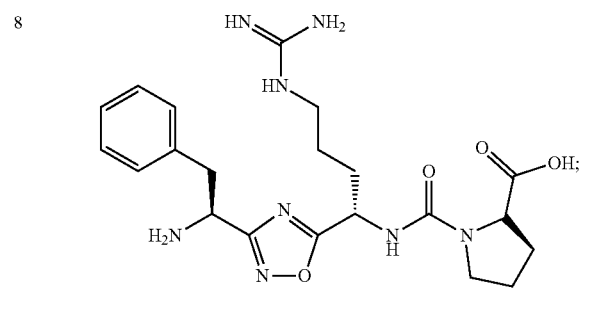 |
| 9 | 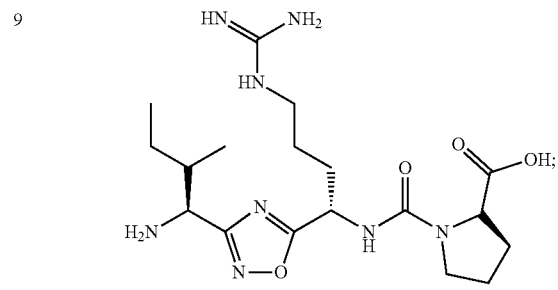 |
| 10 | 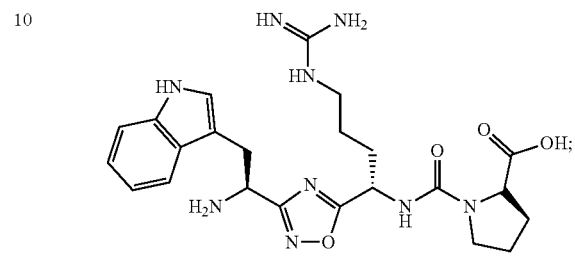 |
| 11 | 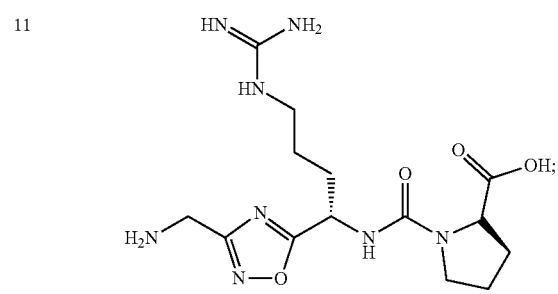 |
| Compound | Structure |
|---|---|
| 12 | 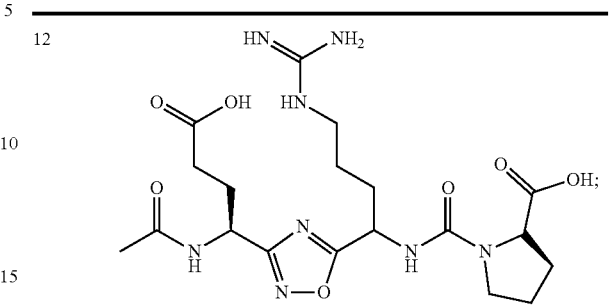 |
| 13 | 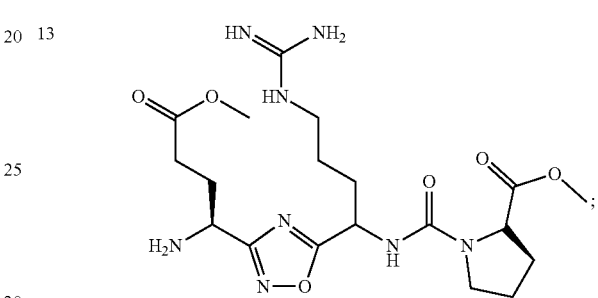 |
| 14 | 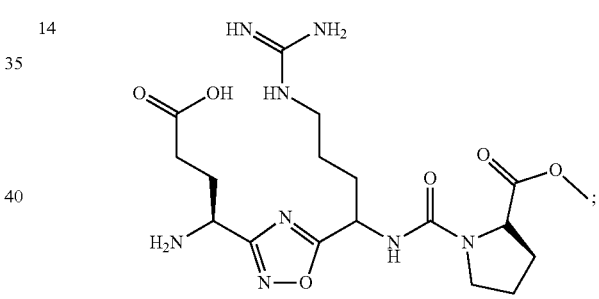 |
| 15 | 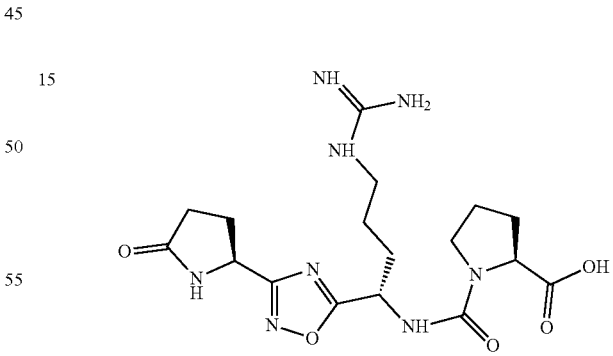 |
or a pharmaceutically acceptable salt or an amide or an ester, or a stereoisomer thereof.
5. A pharmaceutical composition comprising a compound of formula (IA) according to claim 1, and a pharmaceutically acceptable carrier.

6. A compound of the formula:

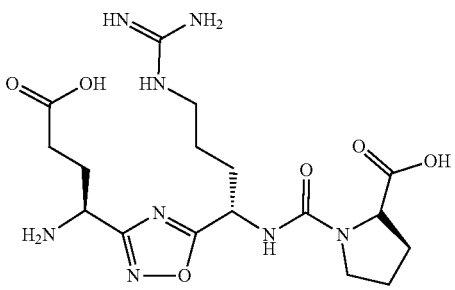

or a pharmaceutically acceptable salt or an amide or an ester, or a stereoisomer thereof.

7. A pharmaceutical composition comprising a compound according to claim 6, and a pharmaceutically acceptable carrier.

8. The compound of claim 6, which is of the formula:

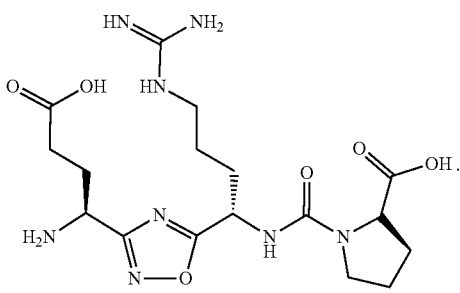

9. The compound of claim 6, which is of the formula:

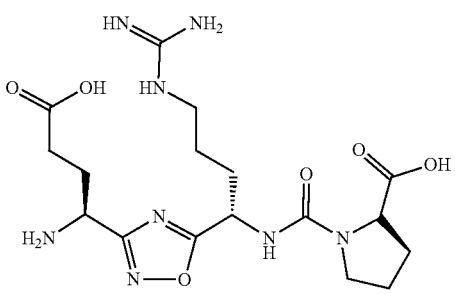

or a pharmaceutically acceptable salt thereof.

10. The compound of claim 6, which is of the formula:

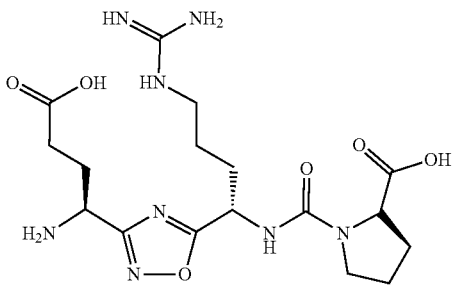

or an amide thereof.

11. The compound of claim 6, which is of the formula:

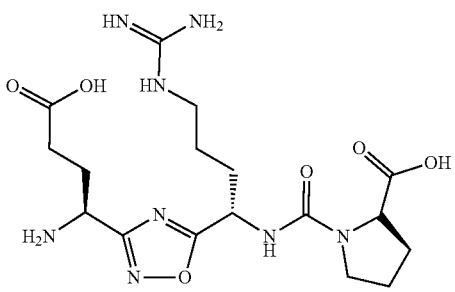

or an ester thereof.

12. The compound of claim 6, which is of the formula:

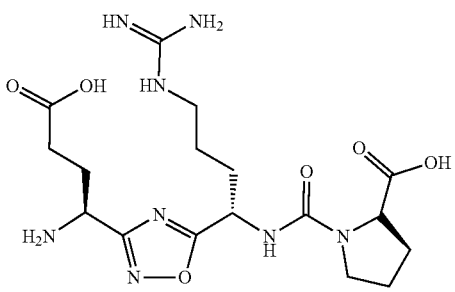

or a stereoisomer thereof.

13. A pharmaceutical composition comprising a compound according to claim 8, and a pharmaceutically acceptable carrier.

14. A pharmaceutical composition comprising a compound according to claim 9, and a pharmaceutically acceptable carrier.

15. A pharmaceutical composition comprising a compound according to claim 10, and a pharmaceutically acceptable carrier.

16. A pharmaceutical composition comprising a compound according to claim 11, and a pharmaceutically acceptable carrier.

17. A pharmaceutical composition comprising a compound according to claim 12, and a pharmaceutically acceptable carrier.

* * * * *

UNITED STATES PATENT AND TRADEMARK OFFICE
CERTIFICATE OF CORRECTION

PATENT NO. : 11,274,123 B2
APPLICATION NO. : 16/245860
DATED : March 15, 2022
INVENTOR(S) : Pottayil Govindan Nair Sasikumar et al.

It is certified that error appears in the above-identified patent and that said Letters Patent is hereby corrected as shown below:

In the Claims

In Claim 4, Column 85, Line 55:
Compound identifier "1" should be replaced with "3";

In Claim 4, Column 86, Line 7:
Compound identifier "2" should be replaced with "5";

In Claim 4, Column 86, Line 18:
Compound identifier "3" should be replaced with "23";

In Claim 4, Column 86, Line 32:
Compound identifier "4" should be replaced with "24";

In Claim 4, Column 86, Line 44:
Compound identifier "5" should be replaced with "25";

In Claim 4, Column 86, Line 55:
Compound identifier "6" should be replaced with "26";

In Claim 4, Column 87, Line 6:
Compound identifier "7" should be replaced with "27";

In Claim 4, Column 87, Line 20:
Compound identifier "8" should be replaced with "28";

In Claim 4, Column 87, Line 33:
Compound identifier "9" should be replaced with "29";

Signed and Sealed this
Ninth Day of January, 2024

*Katherine Kelly Vidal*

Katherine Kelly Vidal
*Director of the United States Patent and Trademark Office*

CERTIFICATE OF CORRECTION (continued)
U.S. Pat. No. 11,274,123 B2

In Claim 4, Column 87, Line 45:
Compound identifier "10" should be replaced with "30";

In Claim 4, Column 87, Line 55:
Compound identifier "11" should be replaced with "31";

In Claim 4, Column 88, Line 6:
Compound identifier "12" should be replaced with "38";

In Claim 4, Column 88, Line 20:
Compound identifier "13" should be replaced with "39";

In Claim 4, Column 88, Line 34:
Compound identifier "14" should be replaced with "40";

In Claim 4, Column 88, Line 47:
Compound identifier "15" should be replaced with "54".